US006344476B1

(12) United States Patent
Ranges et al.

(10) Patent No.: US 6,344,476 B1
(45) Date of Patent: *Feb. 5, 2002

(54) INHIBITION OF P38 KINASE ACTIVITY BY ARYL UREAS

(75) Inventors: Gerald Ranges, Hamden; William Scott, Guilford; Michael Bombara, Hamden; Deborah Rauner, Sandy Hook; Aniko Redman, Derby; Roger Smith, Madison, all of CT (US); Holger Paulsen, Wuppertal (DE); David Gunn; Jinshan Chen, both of Hamden, CT (US); Joel Renick, West Haven, CT (US)

(73) Assignee: Bayer Corporation, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,396

(22) Filed: May 22, 1998

Related U.S. Application Data

(60) Provisional application No. 60/098,557, filed on May 23, 1997.

(51) Int. Cl.$^7$ .................. A61K 31/38; A61K 31/385; A61K 31/34; A61K 31/17
(52) U.S. Cl. .................. 514/447; 514/439; 514/461; 514/588; 514/596
(58) Field of Search ................. 514/588, 590, 514/592, 596, 608, 620, 439, 461, 447, 473

(56) References Cited

U.S. PATENT DOCUMENTS

| 1,742,156 A | 12/1929 | Fitzky |
| 2,046,375 A | 7/1936 | Goldstein et al. |
| 2,093,265 A | 9/1937 | Coffby et al. |
| 2,288,422 A | 6/1942 | Rohm |
| 2,683,082 A | 7/1954 | Hill et al. |
| 2,745,874 A | 5/1956 | Schetty et al. |
| 2,781,330 A | 2/1957 | Downey |
| 2,867,659 A | 1/1959 | Model et al. |
| 2,877,268 A | 3/1959 | Applegate et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,646,059 A | 2/1972 | Brantley |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |

(List continued on next page.)

FOREIGN PATENT DOCUMENTS

| CA | 2146707 | 10/1995 |
| DE | 0 487 014 | 12/1929 |
| DE | 0 511 468 | 10/1930 |
| DE | 0 523 437 | 5/1931 |
| DE | 3305866 A1 | 2/1983 |
| DE | 35 29 747 A1 | 8/1985 |
| DE | 35 40 377 A1 | 11/1985 |
| DE | 0 253 997 | 2/1988 |
| EP | 335156 | 3/1989 |
| EP | 371876 | 11/1989 |
| EP | 0 405 233 | 1/1991 |
| EP | 459887 | 5/1991 |
| EP | 0 502 504 A1 | 9/1992 |
| FR | 1 457 172 | 9/1966 |
| GB | 0 828 231 | 10/1956 |

(List continued on next page.)

OTHER PUBLICATIONS

Dumas, J., "CAS Substructure," May 6, 1997, pp. 1–29.
Scott, Bill, "Substructure (Patent Families)," Aug. 11, 1997, pp. 1–19.
Scott, Bill, "Substructure #2," Nov. 25, 1997, pp. 1–3.
Abstract of EP 116,932 (Date: Aug. 29, 1984).
Abstract of EP 676,395 (Date: Oct. 11, 1995)(U.S. equivalent 5,698,581).
Abstract of EP 202,538 (Date: Nov. 26, 1986).
Abstract of EP 16,371 (Date: Oct. 1, 1980).
Avruch et al., "Raf meets Ras: completing the framework of a signal transduction pathway", TIBS 19; Jul. 1994; pp. 279–2823.
White, A. D., et al., "Heterocyclic Ureas: Inhibitors of Acyl–CoA:Cholesterol O–Acyltransferase as Hypocholesterolemic Agents," Jun. 6, 1996, pp. 4382–4395.
Audia, James E., et al., "Potent, Selective Tetraphdro–β–carboline Antagonists of the Serotonin 2B (5HT$_{2B}$) Contractile Receptor in the Rat Stomach Fundus," Jan. 22, 1996, pp. 2773–2780.
Forbes, Ian T., "N–(1–Methyl–5–indolyl)–N'–(3–methyl–5–isothiazolyl)urea: A Novel, High–Affinity 5–HT$_{2B}$ Receptor Antagonist," Mar. 17, 1995, pp. 855–857.

(List continued on next page.)

*Primary Examiner*—Theodore J. Criares
(74) *Attorney, Agent, or Firm*—Millen, White, Zelano, & Branigan, P.C.

(57) ABSTRACT

This invention relates to the use of a group of aryl ureas in treating cytokine mediated diseases other than cancer and proteolytic enzyme mediated diseases other than cancer, and pharmaceutical compositions for use in such therapy.

18 Claims, No Drawings

U.S. PATENT DOCUMENTS

| | | |
|---|---|---|
| 4,001,256 A | 1/1977 | Callahan et al. |
| 4,009,847 A | 3/1977 | Aldrich et al. |
| 4,062,861 A | 12/1977 | Yukinaga et al. |
| 4,071,524 A | 1/1978 | Banitt |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,405,644 A | 9/1983 | Kabbe et al. |
| 4,410,697 A | 10/1983 | Török et al. |
| 4,437,878 A | 3/1984 | Acker et al. |
| 4,468,380 A | 8/1984 | O'Doherty et al. |
| 4,473,579 A | 9/1984 | Devries et al. |
| 4,511,571 A | 4/1985 | Böger et al. |
| 4,514,571 A | 4/1985 | Nakai et al. |
| 4,526,997 A | 7/1985 | O'Doherty et al. |
| 4,623,662 A | 11/1986 | De Vries |
| 4,643,849 A | 2/1987 | Hirai et al. |
| 4,740,520 A | 4/1988 | Hallenbach et al. |
| 4,760,063 A | 7/1988 | Hallenbach et al. |
| 4,808,588 A | 2/1989 | King |
| 4,820,871 A | 4/1989 | Kissener et al. |
| 4,863,924 A | 9/1989 | Haga et al. |
| 4,983,605 A | 1/1991 | Kondo et al. |
| 4,985,449 A | 1/1991 | Haga et al. |
| 5,036,072 A | 7/1991 | Nakajama et al. |
| 5,059,614 A | 10/1991 | Lepage et al. |
| 5,098,907 A | 3/1992 | Kondo et al. |
| 5,130,331 A | 7/1992 | Pascual |
| 5,162,360 A | 11/1992 | Creswell et al. |
| 5,312,820 A | 5/1994 | Ashton et al. |
| 5,319,099 A | 6/1994 | Kamata et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,470,882 A | 11/1995 | Dixon et al. |
| 5,500,424 A | 3/1996 | Nagamine et al. |
| 5,508,288 A | 4/1996 | Forbes et al. |
| 5,597,719 A | 1/1997 | Freed et al. |
| 5,696,138 A | 12/1997 | Olesen et al. |
| 5,698,581 A | 12/1997 | Kleemann et al. |
| 5,773,549 A | 6/1998 | Tang et al. |
| 5,780,483 A | 7/1998 | Widdowson et al. |
| 5,807,891 A | 9/1998 | Bold et al. |

FOREIGN PATENT DOCUMENTS

| | | |
|---|---|---|
| GB | 0 771 333 | 3/1957 |
| GB | 0 921 682 | 3/1963 |
| GB | 50-149668 | 11/1975 |
| GB | 1590870 | 6/1981 |
| JP | 44 2569 | 2/1969 |
| JP | 50-76072 | 6/1975 |
| JP | 50-77375 | 6/1975 |
| JP | 51 063170 | 1/1976 |
| JP | 51-80862 | 7/1976 |
| JP | 53 086033 | 7/1978 |
| JP | 55 98152 | 7/1980 |
| JP | 55-124763 | 9/1980 |
| JP | 55-162772 | 12/1980 |
| JP | 3 532 47 | 3/1991 |
| WO | 96/02112 | 3/1990 |
| WO | 93/18028 | 9/1993 |
| WO | 93/24458 | 12/1993 |
| WO | 94/14801 | 7/1994 |
| WO | 94/18170 | 8/1994 |
| WO | 94 22807 | 10/1994 |
| WO | 94/25012 | 11/1994 |
| WO | 95/02591 | 1/1995 |
| WO | 95/07922 | 3/1995 |
| WO | 95/13067 | 5/1995 |
| WO | 95/31451 | 11/1995 |
| WO | 95/33458 | 12/1995 |
| WO | 96/25157 A1 | 8/1996 |
| WO | 96/40673 | 12/1996 |
| WO | A1 96/40675 | 12/1996 |
| WO | 97/29743 | 8/1997 |
| WO | 97/40028 A1 | 10/1997 |
| WO | 97/45400 | 12/1997 |
| WO | 97/49399 | 12/1997 |
| WO | 97/49400 | 12/1997 |
| WO | 98/22432 | 5/1998 |
| WO | 99/00357 | 1/1999 |
| WO | 99/00370 | 1/1999 |
| WO | WO 00/17175 | 9/1999 |

OTHER PUBLICATIONS

Boulton, A. J., et al., "Heterocyclic Rearrangements. Part X.[1] A Generalised Monocyclic Rearrangement," 1967, 2005–2007.

N. S. Magnuson, et al., "The Raf–1 serine/threonine protein kinase," Cancer Biology, vol. 5, 1994, pp. 247–253.

G. Daum, et al., The ins and outs of Raf Kinases,: TIBS 19, Nov. 1994, pp. 474–480.

W. Kolch, et al., "Raf–1 protein kinase is required for growth of induced NIH/3T3 cells," Letters to Nature, vol. 349, Jan. 31, 1991, pp. 226–228.

M. Fridman, et al., "The Minimal Fragments of c–Raf–1 and NF1 That Can Suppress v–Ha–Ras–Induced Malignant Phenotype," The Journal of Biological Chemistry, vol. 269, No. 48, Dec. 2, 1994, pp. 30105–30108.

G. L. Bolton, et al., Chapter 17. Ras Oncogene Directed Approaches in Cancer Chemotherapy, Annual Reports In Medicinal Chemistry, vol. 29, 1994, pp. 165–174.

J. L. Bos, "ras Oncogenes in Human Cancer: A Review," Cancer Research, vol. 49, Sep. 1, 1989, pp. 4682–4689.

Michaelis, Justus, Liebigs Ann. Chem. (JLACBF) 397, 1913, 143.

B. P. Monia, et al., "Antitumor activity of a phosphorothioate antisense oligodeopxynucleotide targeted against C–raf kinase," Nature Medicine, vol. 2, No. 6, Jun. 1996, pp. 668–675.

Lee, et al., Bicyclic Imidazoles as a Novel Class of Cytokine Biosynthesis Inhiibitors, N.Y. Academy of Science, 1993, pp. 149–170.

F. Lepage, et al., "New N–aryl isoxazolecarboxamides and N–isoxazolybenzamides as anticonvulsant agents," Eur. J. Med. Chem, vol. 27, 1992, pp. 581–593.

Ridley, et al., "Actions of IL–1 are Selectively Controlled by p38 Mitogen–Activated Protein Kinase," The American Association of Immunologists, 1997, p. 3165–73.

Chemical Abstract, vol. 116, No. 21, May 25, 1992, pp. 741–742.

Tarzia, G. et al. Whythesis and anti–inflammatory properties of some pyrrolo(1H,3H)[3,4]pyrimidin–2–ones and pyrrolo(1H,3H)[3,4–d]pyurimidin–2–ones and pyrrolo(1H, 3H)–pyrimidin–2–ones. Chemical Abstracts. Aug. 27, 1979, No. 74558p; p. 594.

T. Murata et al., "Facile synthesis of new pyrrolo[3,4–d] pyrimidine–2,4–diones", Chemical and Pharmaceutical Bulletin, vol. 22, 1974, pp. 1212–1213 (XP–000973679).

M. T. Garcia–Lopez et al., "New routes for the synthesis of pyrrolo[3,2–d]– and –[2,3–d]–pyrimidine systems starting from a common pyrrole derivative", Journal of the Chemical Society, Perkin Trans. 1, vol. 1978, 1978, pp. 483–487 (XP–000973638).

Abstract of EP 16,371 (Date: Oct. 1, 1980).

INHIBITION OF P38 KINASE ACTIVITY BY ARYL UREAS

CLAIM OF DOMESTIC PRIORITY UNDER 35 U.S.C. 119(e)

Priority is claimed under 35 U.S.C. 119(e) of provisional application Ser. No. 60/098,557 of May 23, 1997.

FIELD OF THE INVENTION

This invention relates to the use of a group of aryl ureas in treating cytokine mediated diseases and proteolytic enzyme mediated diseases, and pharmaceutical compositions for use in such therapy.

BACKGROUND OF THE INVENTION

Two classes of effector molecules which are critical for the progression of rheumatoid arthritis are pro-inflammatory cytokines and tissue degrading proteases. Recently, a family of kinases was described which is instrumental in controlling the transcription and translation of the structural genes coding for these effector molecules.

The MAP kinase family is made up of a series of structurally related proline-directed serine/threonine kinases which are activated either by growth factors (such as EGF) and phorbol esters (ERK), or by IL-1, TNFα or stress (p38, JNK). The MAP kinases are responsible for the activation of a wide variety of transcription factors and proteins involved in transcriptional control of cytokine production. A pair of novel protein kinases involved in the regulation of cytokine synthesis was recently described by a group from Smith-Kline Beecham (Lee et al. *Nature* 1994, 372, 739). These enzymes were isolated based on their affinity to bond to a class of compounds, named CSAIDs cytokine suppressive anti-inflammatory drugs) by SKB. The CSAIDs, pyridinyl imidazoles, have been shown to have cytokine inhibitory activity both in vitro and in vivo. The isolated enzymes, CSBP-1 and -2 (CSAID binding protein 1 and 2) have been cloned and expressed. A murine homologue for CSBP-2, p38, has also been reported (Han et al. *Science* 1994, 265, 808).

Early studies suggested that CSAIDs function by interfering with m-RNA translational events during cytokine biosynthesis. Inhibition of p38 has been shown to inhibit both cytokine production (eg., TNFα, IL-1, IL-6, IL-8; Lee et al. *N.Y. Acad. Sci.* 1993, 696, 149) and proteolytic enzyme production (eg., MMP-1, MMP-3; Ridley et al. *J. Immunol.* 1997, 158, 3165) in vitro and/or in vivo.

Clinical studies have linked TNFα production and/or signaling to a number of diseases including rheumatoid arthritis (Maini. *J. Royal Coll. Physicians London* 1996, 30, 344). In addition, excessive levels of TNFα have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoporosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995–6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immmunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including Plasmodium falciparum malaria (Perlmann et al. *Infect. Immunit.* 1997, 65, 116) and cerebral malaria (Rudin et al. *Am. J. Pathol.* 1997, 150, 257), non-insulin-dependent diabetes mellitus (NIDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). THFα levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). THFα has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from Staphylococcus infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

Because inhibition of p38 leads to inhibition of TNFα production, p38 inhibitors will be useful in treatment of the above listed diseases.

A number of diseases are mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), dystrophobic epidermolysis bullosa (Kronberger et al. *J. Invest. Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of MMP production, p38 inhibitors will be useful in treatment of the above listed diseases.

Inhibitors of p38 are active in animal models of TNFα production, including a murine lipopolysaccharide (LPS) model of TNFα production. Inhibitors of p38 are active in a number of standard animal models of inflammatory diseases, including carrageenan-induced edema in the rat paw, arachadonic acid-induced edema in the rat paw, arachadonic acid-induced peritonitis in the mouse, fetal rat long bone resorption, murine type II collagen-induced arthritis, and Fruend's adjuvant-induced arthritis in the rat. Thus, inhibitors of p38 will be useful in treating diseases mediated by one or more of the above-mentioned cytokines and/or proteolytic enzymes.

The need for new therapies is especially important in the case of arthritic diseases. The primary disabling effect of osteoarthritis, rheumatoid arthritis and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. P38 inhibitors will halt or reverse the progression of cartilage loss and obviate or delay surgical intervention.

Several patents have appeared claiming polyarylimidazoles and/or compounds containing polyarylimidazoles as inhibitors of p38 (for example, Lee et al. WO 95/07922; Adams et al. WO 95/02591; Adams et al. WO 95/13067; Adams et al. WO 95/31451). It has been reported that arylimidazoles complex to the ferric form of cytochrome $P450_{cam}$ (Harris et al. *Mol. Eng.* 1995, 5, 143, and references therein), causing concern that these compounds may display structure-related toxicity (Howard-Martin et al. *Toxicol Pathol.* 1987, 15, 369). Therefore, there remains a need for improved p38 inhibitors.

SUMMARY OF THE INVENTION

This invention provides compounds, generally described as aryl ureas, including both aryl and heteroaryl analogues, which inhibit p38 mediated events and thus inhibit the production of cytokines (such as TNFα, IL-1 and IL-8) and proteolytic enzymes (such as MMP-1 and MMP-3). The invention also provides a method of treating a cytokine mediated disease state in humans or mammals, wherein the cytokine is one whose production is affected by p38. Examples of such cytokines include, but are not limited to TNFα, IL-1 and IL-8. The invention also provides a method of treating a protease mediated disease state in humans or mammals, wherein the protease is one whose production is affected by p38. Examples of such proteases include, but are not limited to collagenase (MMP-1) and stromelysin (MMP-3).

Accordingly, these compounds are useful therapeutic agents for such acute and chronic inflammatory and/or immunomodulatory diseases as rheumatoid arthritis, osteoarthritis, septic arthritis, rheumatic fever, bone resorption, postmenopausal osteoporosis, sepsis, gram negative sepsis, septic shock, endotoxic shock, toxic shock syndrome, systemic inflammatory response syndrome, inflammatory bowel diseases including Crohn's disease and ulcerative colitis, Jarisch-Herxheimer reactions, asthma, adult respiratory distress syndrome, acute pulmonary fibrotic diseases, pulmonary sarcoidosis, allergic respiratory diseases, silicosis, coal worker's pneumoconiosis, alveolar injury, hepatic failure, liver disease during acute inflammation, severe alcoholic hepatitis, malaria including Plasmodium falciparum malaria and cerebral malaria, non-insulin-dependent diabetes mellitus (NIDDM), congestive heart failure, damage following heart disease, atherosclerosis, Alzheimer's disease, acute encephalitis, brain injury, multiple sclerosis (MS) including demyelation and oligiodendrocyte loss in multiple sclerosis, advanced cancer, lymphoid malignancies, tumor metastasis, pancreatitis, including systemic complications in acute pancreatitis, impaired wound healing in infection, inflammation and cancer, periodontal diseases, corneal ulceration, proteinuria, myelodysplastic syndromes, systemic lupus erythematosus, biliary cirrhosis, bowel necrosis, psoriasis, radiation injury, toxicity following administration of monoclonal antibodies such as OKT3, host-versus-graft reactions including ischemia reperfusion injury and allograft rejections including kidney, liver, heart, and skin allograft rejections, lung allograft rejection including chronic lung allograft rejection (obliterative bronchitis) as well as complications due to total hip replacement, and infectious diseases including tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from Staphylococcus infection, meningococcal infection, and infections from *Borrelia burgdorferi, Treponema pallidum,* cytomegalovirus, influenza virus, Theiler's encephalomyelitis virus, and the human immunodeficiency virus (HIV).

Accordingly, the present invention is directed to a method for the treatment of diseases mediated by p38, e.g., mediated by one or more cytokines or proteolytic enzymes produced and/or activated by a p38 mediated process, comprising administering a compound of Formula I,

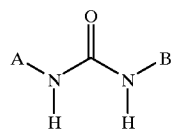
I wherein

A is $C_{6-2}$-aryl or $C_{5-12}$-heteroaryl, each optionally substituted, e.g. by $C_{1-4}$-alkyl, $C_{3-6}$-cycloalkyl, halogen, —OH, —OR$^1$, —NR$^1_2$;

B is

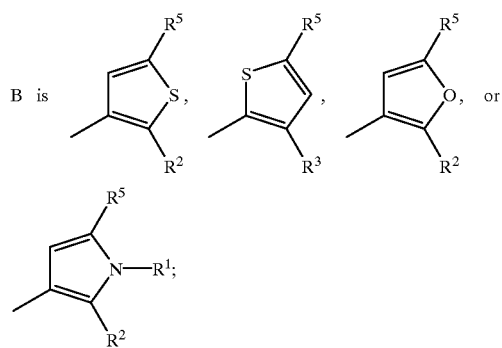

$R^1$ is H or $C_{1-4}$-alkyl;
$R^2$ and $R^3$ are each independently halogen, —COOR$^1$, —CN, —CONR$^7$R$^8$, or —CH$_2$NHR$^9$;
$R^5$ is $C_{3-5}$-alkyl;
$R^6$ is $C_{1-6}$-alkyl;
$R^7$ is hydrogen;
$R^8$ is methyl;
$R^9$ is hydrogen, methyl or —CO—R$^{10}$; and
$R^{10}$ is hydrogen or methyl optionally substituted by NR$^6_2$ or COOR$^6$.

In Formula I, suitable heteroaryl groups A include, but are not limited to, 5–10 carbon-atom aromatic rings or ring systems containing 1–2 rings, at least one of which is aromatic, in which one or more, e.g., 1–4 carbon atoms in one or more of the rings can be replaced by oxygen, nitrogen or sulfur atoms. Each ring typically has 5–6 atoms. For example, A can be 2- or 3-thienyl, 1,3,4-thiadiazol-2- or -5-yl, 7-indolyl, or 8-quinolinyl, or additionally optionally substituted phenyl, 2- or 3-thienyl, 1,3,4-thiadiazolyl, etc. For example, A can be 4-methylphenyl, 4-fluorophenyl, 5-methyl-2-thienyl, 4-methyl-2-thienyl or 5-cyclopropyl-1,3,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

Suitable cycloalkyl groups include cyclopropyl, cyclobutyl, cyclopentyl, cyclohexyl, etc.

Suitable aryl groups include, for example, phenyl and 1- and 2-naphthyl.

Suitable halogen groups include F, Cl, Br, and/or I, from one to per-substitution (i.e. all H atoms on a group replaced by a halogen atom) being possible, mixed substitution of halogen atom types also being possible on a given moiety.

Preferred compounds of Formula I include those where $R^2$ or $R^3$ is —COOR$^1$ or —CONR$^7$R$^8$; $R^1$ is $C_{1-4}$-alkyl; $R^7$ is H; and $R^8$ is methyl, and those where $R^5$ is isopropyl or tert-butyl.

The invention also relates to compounds per se, of Formula II

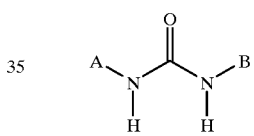
II wherein

A is $C_{6-12}$-aryl or $C_{5-12}$-heteroaryl, each optionally substituted, e.g., by $C_{1-4}$-alkyl, $C_{3-6}$-cycloalkyl, halogen, —OH, —OR$^1$, —NR$^1_2$;

B is

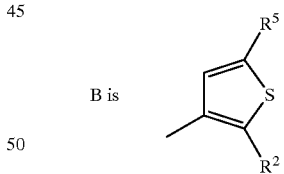

$R^1$ is H or $C_{1-4}$-alkyl;
$R^2$ is —COOR$^1$, —CONR$^7$R$^8$, or —CH$_2$NHR$^9$;
$R^5$ is $C_{3-5}$-alkyl;
$R^6$ is $C_{1-6}$-alkyl;
$R^7$ is H;
$R^8$ is methyl;
$R^9$ is hydrogen, methyl or —CO—R$^{10}$; and
$R^{10}$ is hydrogen or methyl optionally substituted by NR$^6_2$ or COOR$^6$,
with the provisos that A is not unsubstituted naphthyl; and if A is unsubstituted phenyl,
$R^2$ is —COOR$^1$ or —COONR$^7$R$^8$, $R^1$ is $C_{2-4}$-alkyl, and $R^5$ is isopropyl or tert-butyl.

The invention also relates to compounds of Formula III

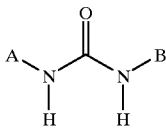

III wherein
A is $C_{6-12}$-aryl or $C_{5-12}$-heteroaryl, each optionally substituted, e.g., by $C_{1-4}$-alkyl, $C_{3-6}$-cycloalkyl, halogen, —OH, —$OR^1$, —$NR^1_2$;

B is 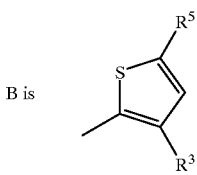

$R^1$ is H or $C_{1-4}$-alkyl;
$R^3$ is —$COOR^1$, —$CONR^7R^8$, or —$CH_2NHR^9$;
$R^5$ is $C_{3-5}$-alkyl;
$R^6$ is $C_{1-6}$-alkyl;
$R^7$ is H;
$R^8$ is methyl;
$R^9$ is hydrogen, methyl or —CO—$R^{10}$; and
$R^{10}$ is hydrogen or methyl optionally substituted by $NR^6_2$ or $COOR^6$,
with the provisos that:
(a) A is not unsubstituted naphthyl;
(b) if A is unsubstituted phenyl, then $R^3$ is —$COOR^1$ or —$CONR^7R^8$, and $R^5$ is isopropyl or tert-butyl; and
if $R^5$ is isopropyl, then A is not phenyl substituted by halogen, or —$OR^1$.

The invention further relates to compounds of Formula IV

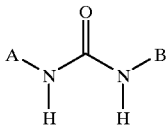

IV wherein
A is $C_{6-12}$-aryl or $C_{5-12}$-heteroaryl, each optionally substituted, e.g., by $C_{1-4}$-alkyl, $C_{3-6}$-cycloalkyl, halogen, —OH, —$OR^1$, —$NR^1_2$;

B is 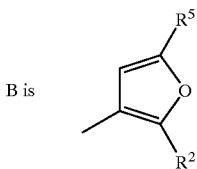

$R^1$ is H or $C_{1-4}$-alkyl;
$R^2$ is —$COOR^1$, —$CONR^7R^8$, or —$CH_2NHR^9$;
$R^5$ is $C_{3-5}$-alkyl;
$R^6$ is $C_{1-6}$-alkyl;
$R^7$ is H;
$R^8$ is methyl;
$R^9$ is hydrogen, methyl or —CO—$R^{10}$; and
$R^{10}$ is hydrogen or methyl optionally substituted by $NR^6_2$ or $COOR^6$,
with the proviso that if A is unsubstituted phenyl, $R^2$ is $COOR^1$ or —$CONR^7R^8$, $R^1$ is $C_{2-4}$-alkyl, and $R^5$ is isopropyl or tert-butyl.

The invention further includes compounds of Formula V

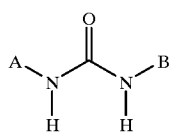

V wherein
A is $C_{6-12}$-aryl or $C_{5-12}$-heteroaryl, each optionally substituted, e.g., by $C_{1-4}$-alkyl, $C_{3-6}$-cycloalkyl, halogen, —OH, —$OR^1$, —$NR^1_2$;

B is 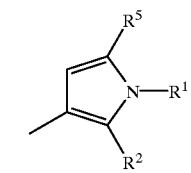

$R^1$ is H or $C_{1-4}$-alkyl;
$R^2$ is —$COOR^1$, —$CONR^7R^8$, or —$CH_2NHR^9$;
$R^5$ is $C_{3-5}$-alkyl;
$R^6$ is $C_{1-6}$-alkyl;
$R^7$ is H;
$R^8$ is methyl;
$R^9$ is hydrogen, methyl or —CO—$R^{10}$; and
$R^{10}$ is hydrogen or methyl optionally substituted by $NR^6_2$ or $COOR^6$.

The present invention is also directed to pharmaceutically acceptable salts of Formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts of Formula I may be formed with a pharmaceutically acceptable cation, for instance, in the case when a substituent group comprises a carboxy moiety. Suitable pharmaceutically suitable cations are well known to those skilled in the art, and include alkaline cations (such as $Li^+$ $Na^+$ or $K^+$), alkaline earth cations (such as $Mg^{+2}$, $Ca^{+2}$ or $Ba^{+2}$), the ammonium cation, and organic cations, including aliphatic and aromatic substituted ammonium, and quaternary ammonium cations such as those arising from triethylamine, N,N-diethylamine, N,N-dicyclohexylamine, pyridine, N,N-dimethylaminopyridine, 1,4-diazabicyclo[2.2.2]octane (DABCO), 1,5-diazabicyclo[4.3.0]non-5-ene (DBN) and 1,8-diazabicyclo[5.4.0]undec-7-ene (DBU).

The compounds of Formulae I–V are either known in the art or may be prepared by use of known chemical reactions and procedures. Nevertheless, the following general preparative methods are presented to aid one of skill in the art in synthesizing the inhibitors of the invention, with more detailed particular examples being presented in the experimental section.

General Preparative Methods

Methyl 5-alkyl-3-aminothiophene-2-carboxylates may be generated by the reaction of methyl thioglycolate with 2-alkyl-2-chloroacrylonitrile in the presence of a base, preferably NaOMe (Ishizaki et al. JP 6025221; Method A). Urea formation may involve either treatment of the thus formed amine with an isocyanate, or an isocyanate equivalent (Method A), or the conversion of the amine into an isocyanate or an isocyanate equivalent by treatment with phosgene or a phosgene equivalent, followed by reaction with a second amine (Method B).

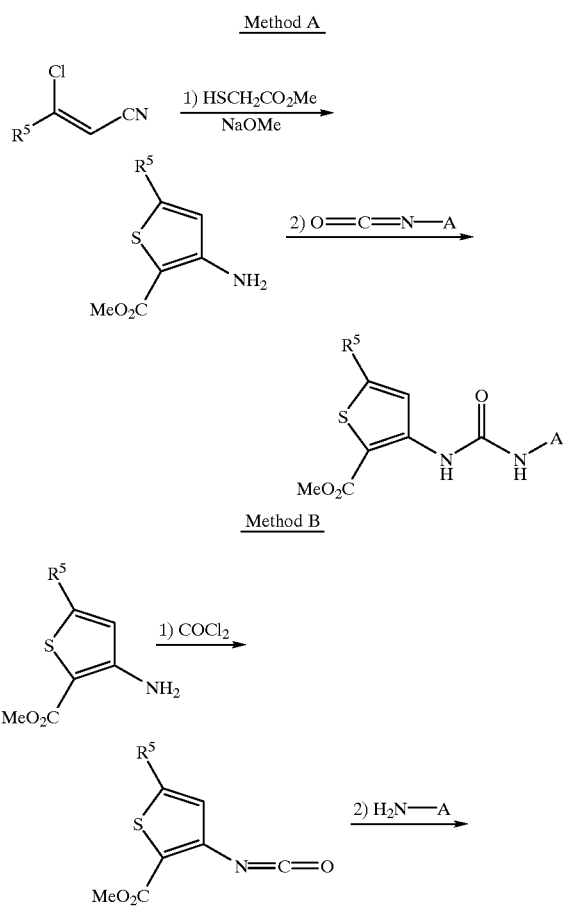

If one or more of the aryl groups is substituted with $NO_2$, or its equivalent, this moiety may be reduced either using catalytic hydrogenation, eg. with $H_2$ and palladium-on-carbon, or using a hydride reagent, eg. $KBH_4$ with CuCl, to give the corresponding amine (Method C).

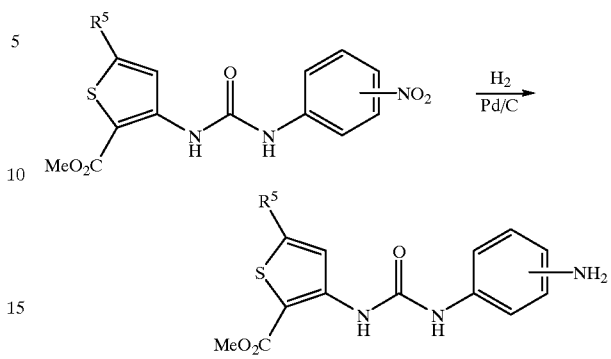

Transesterification of the urea may undertaken in alcohol solvent using a Lewis acid catalyst, eg. titanium alkoxide, (Method D).

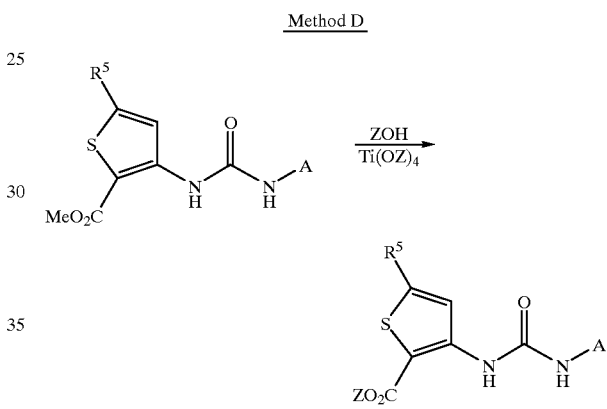

Alternatively, protection of the amine, eg. as the tert-butyl carbamate, followed by saponification of the ester affords the corresponding amino-protected carboxylic acid (Method E). Ester formation may employ one of a wide variety of standard protocols, eg. carbodiimide-mediated coupling, depending on the amine protecting group. Finally, deprotection, for example using an acid source such as HCl or trifluoroacetic acid for the tert-butyl carbamate, followed by urea formation, as illustrated in either Method A or Method B, will generate ester analogues.

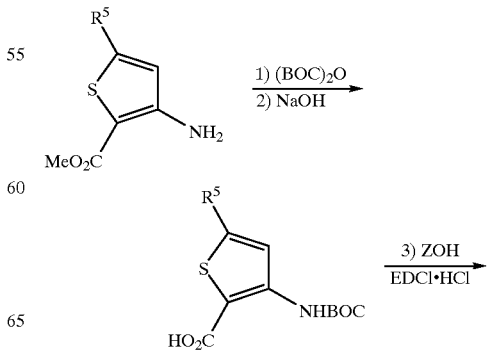

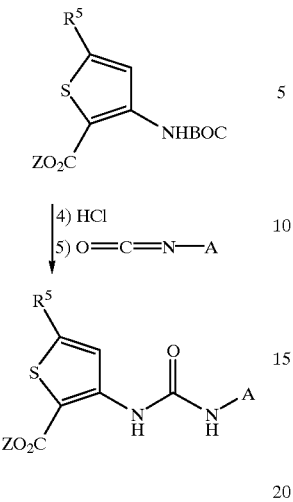

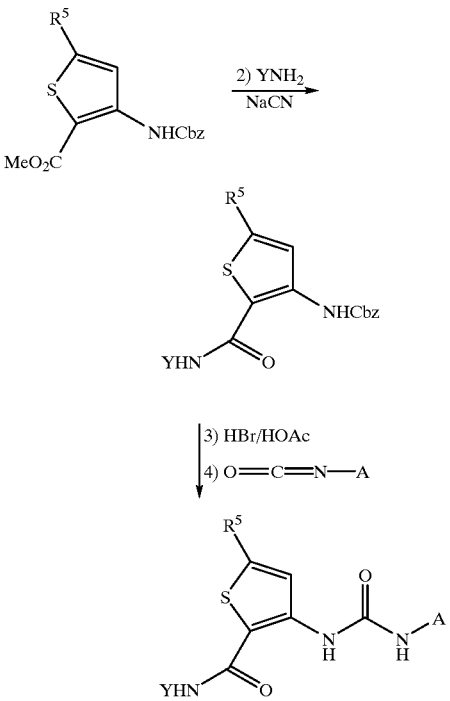

Amide analogues may be generated in a manner similar to that disclosed in Method E. Protection of the amine, eg. as the benzyl carbamate, followed by amide formation, eg. using an amine in the presence of catalytic cyanide, gives the protected amide (Method F). Deprotection, for example with HBr/acetic acid or catalytic hydrogenation for the benzyl carbamate, followed by urea formation as illustrated in Method A will generate amide analogues.

Method F

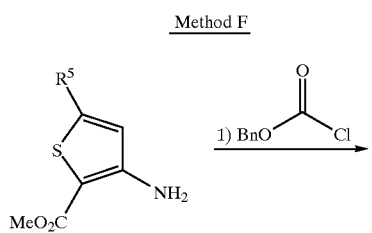

Saponfication of 3-aminothiophene-2-carboxylate esters (eg. with KOH) affords the carboxylic acid, which on treatment with phosgene or a phosgene equivalent gives the 2H-thieno[3,2-d]oxazine-2,4(1H)-dione (Method R). Reaction of the thienooxazine with an aryl amine then affords the substituted 2-carboxythienyl urea. Activation, eg. with SOCl$_2$, followed by treatment with an alcohol affords the corresponding ester. Alternately, treatment of the activated intermediate with a primary or secondary amine affords the corresponding amide.

Method R

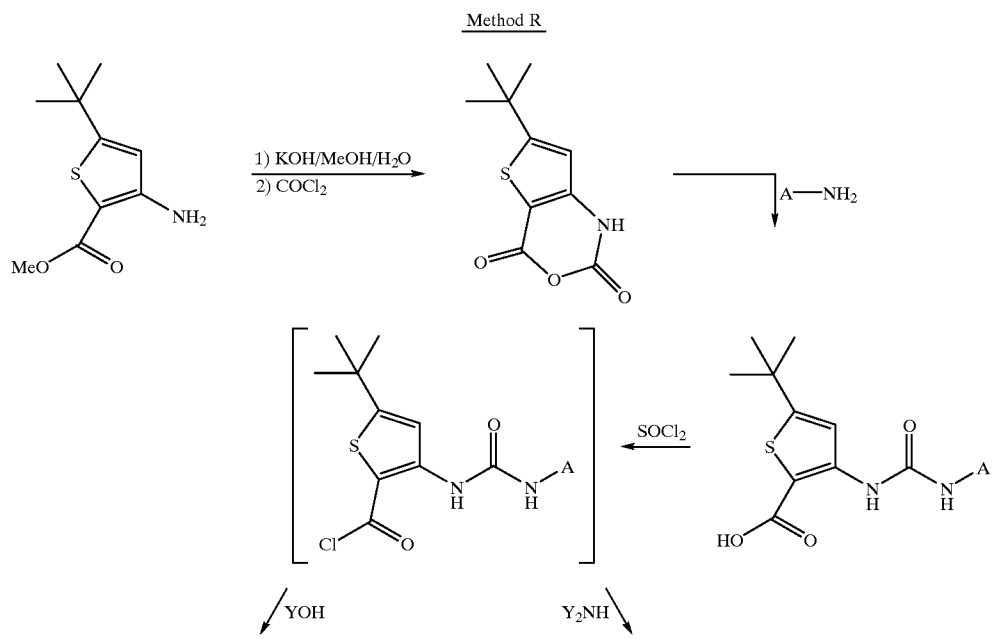

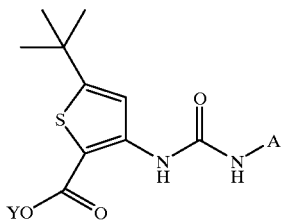
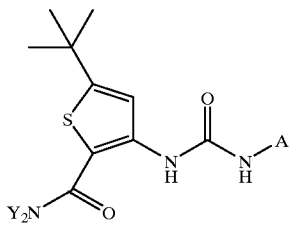

Amide analogues may also be generated by direct treatment of the methyl ester with an aluminum amide (Method G), followed by urea formation as illustrated in Method A.

Method H

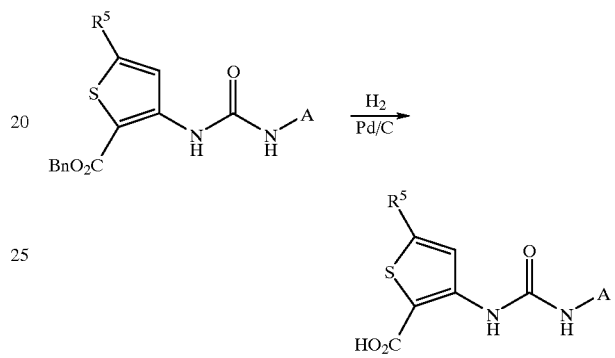

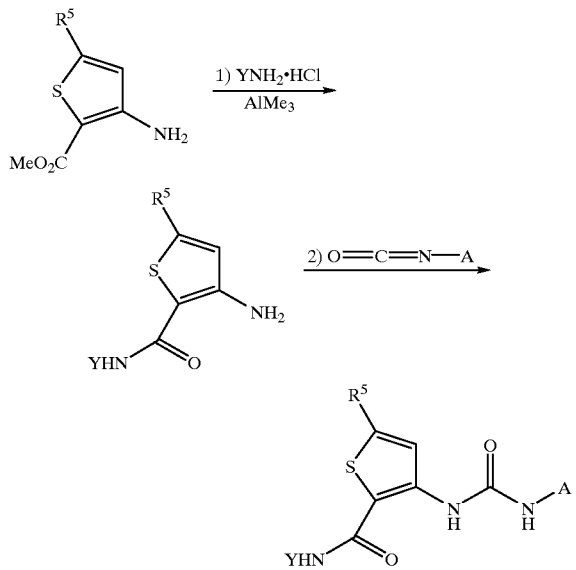

Method G

Ureas containing primary amides may be reduced to the aminomethyl analogues using, for example a $BH_3 \cdot THF$ solution (Method I). The thus generated amine may then be functionalized as desired. Amide formation may be achieved using acid chlorides or their equivalent, or through standard coupling protocols. For example, the amine may be coupled with an amino-protected glycine, eg. N-BOC-glycine, in the presence of a carbodiimide catalyst, eg. DCC, followed by standard removal of the protecting group, for example using an acid source such as HCl or trifluoroacetic acid for the tert-butyl carbamate (Method I).

Method I

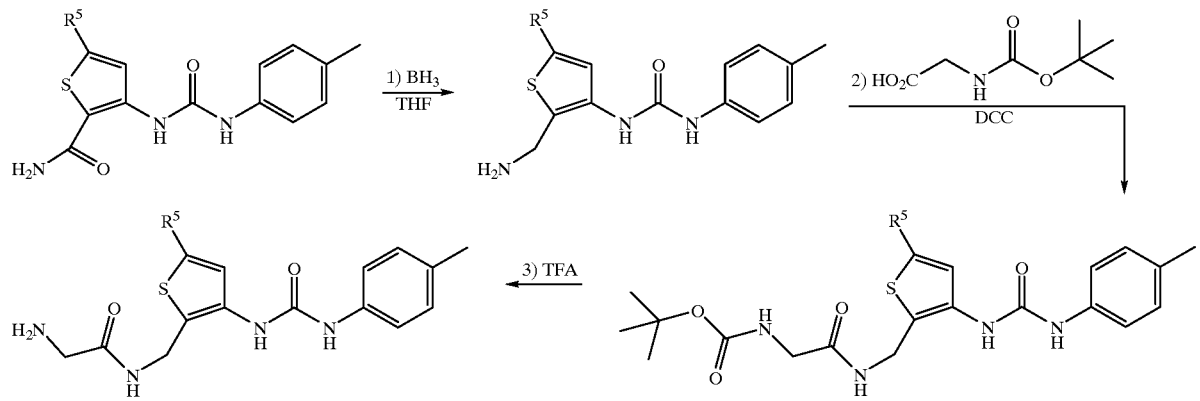

Generation of carboxylic acid analogues may be achieved by hydrolysis of the corresponding esters. For example, catalytic hydrogenation of the C-2 benzyl ester, eg. using $H_2$ and palladium-on-carbon, provides the thiophene-2-carboxylic acid (Method H).

Suitable amines (A—$NH_2$ with A as in Formulae I–V) may be commercially available, or may be generated through any amine forming reaction, such as use of any variation of the Schmidt rearrangement. Thus, for example, a carboxylic acid may be treated with a phosgene equivalent, such as ethyl chloroformate, and an azide source to generate the isocyanate (Method J). The isocyanate may be treated with water to afford the corresponding amine, or directly reacted with a second amine to afford a urea (Method J).

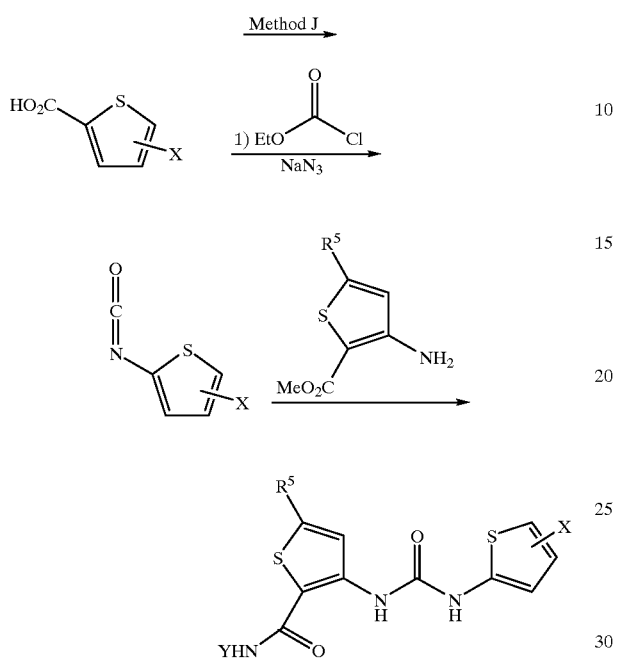

Lithiation of 2-alkylfurans, using for example n-BuLi, followed by quenching of the 2-furyllithium with $CO_2$ affords the furan-2-carboxylic acid (Method K). Dianion formation, using for example n-BuLi, followed by reaction with tosyl azide, then treatment with a diazomethane equivalent gives the azido ester. Finally, furan analogues of methyl 5-alkyl-3-aminothiophene-2-carboxylates may be generated by reduction of the azide, for example with $H_2$ and palladium-on-carbon (Method K). The aminofuran analogues may be converted into ureas in a similar manner to that illustrated in either Method A or Method B.

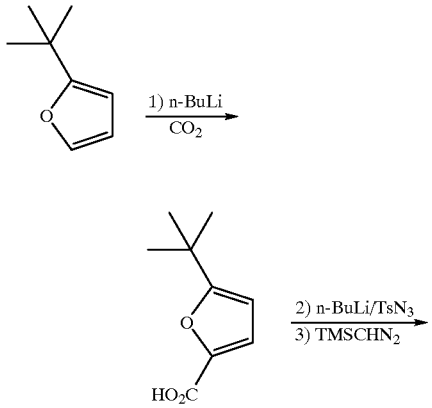

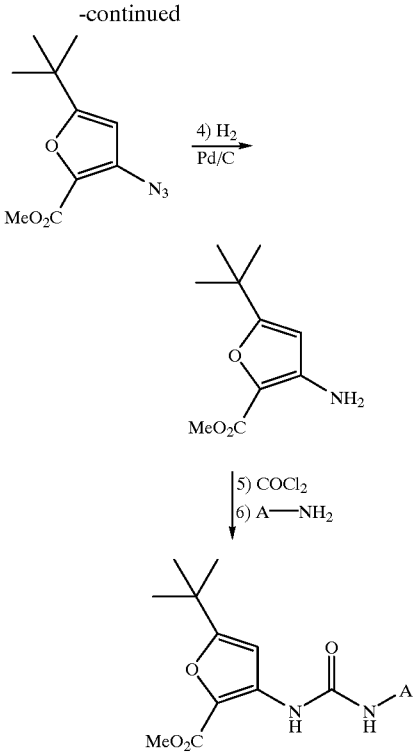

5-Alkyl-3-aminofuran-2-carboxylate esters may also be generated by the reaction of methyl glycolate with 2-alkyl-2-chloroacrylonitrile in the presence of a base (Method L-1). Alternatively, 5-alkyl-3-aminofuran-2-carboxylate esters may be generated from α-cyanoketones (Method L-2). For example, treatment of an α-cyanoketones with an alkyl glycolate under Mitsunobu conditions (eg. triphenylphosphine and a dialkyl azodicarboxylate) affords the β-cyano enol ether. Treatment of the enol ether with a suitable base, such as KOBu-t, NaH, or 1,8-diazabicyclo[5.4.0]undec-7-ene (DBU), then generates the desired aminofuran. Aminofuran analogues may be converted into ureas in a similar manner to that illustrated in either Method A or Method B.

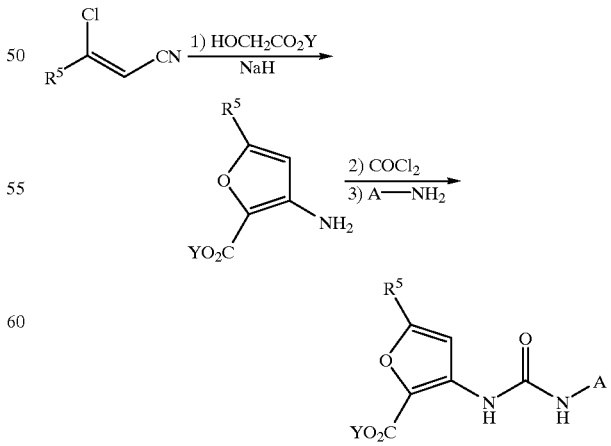

Method L-2

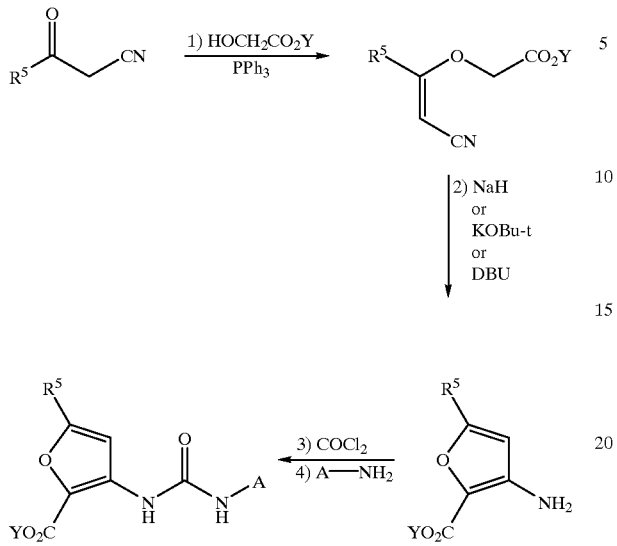

Amide analogues of aminofurancarboxylic acids may be generated by direct treatment of the methyl ester (from L-1 or L-2) with an aluminum amide (Method M), followed by urea formation as illustrated in Method A.

Method M

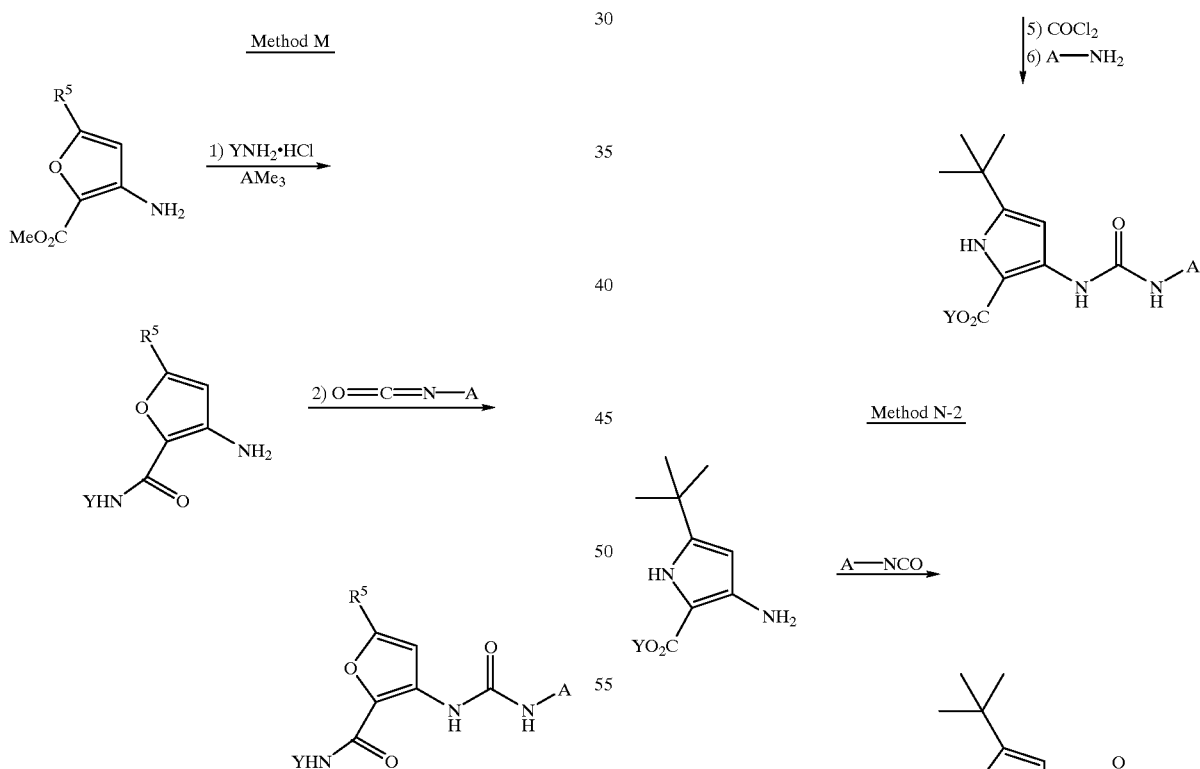

Esterification of pyrrole-2-carboxylic acid followed by Friedel-Crafts alkylation affords the 5-alkyl analogue (Method N-1). Electrophilic nitration of the pyrrole with nitric acid in sulfuric acid affords a separable mixture of the 3-nitro compound shown below and the 3,4-dinitro analogue (Method N-1). Reduction of the nitro group, for example using hydrogen and palladium-on-carbon, affords the amine, which may be converted into the urea in a manner similar to that illustrated in Method B (Method N-1), or on treatment with an isocyanate (Method N-2).

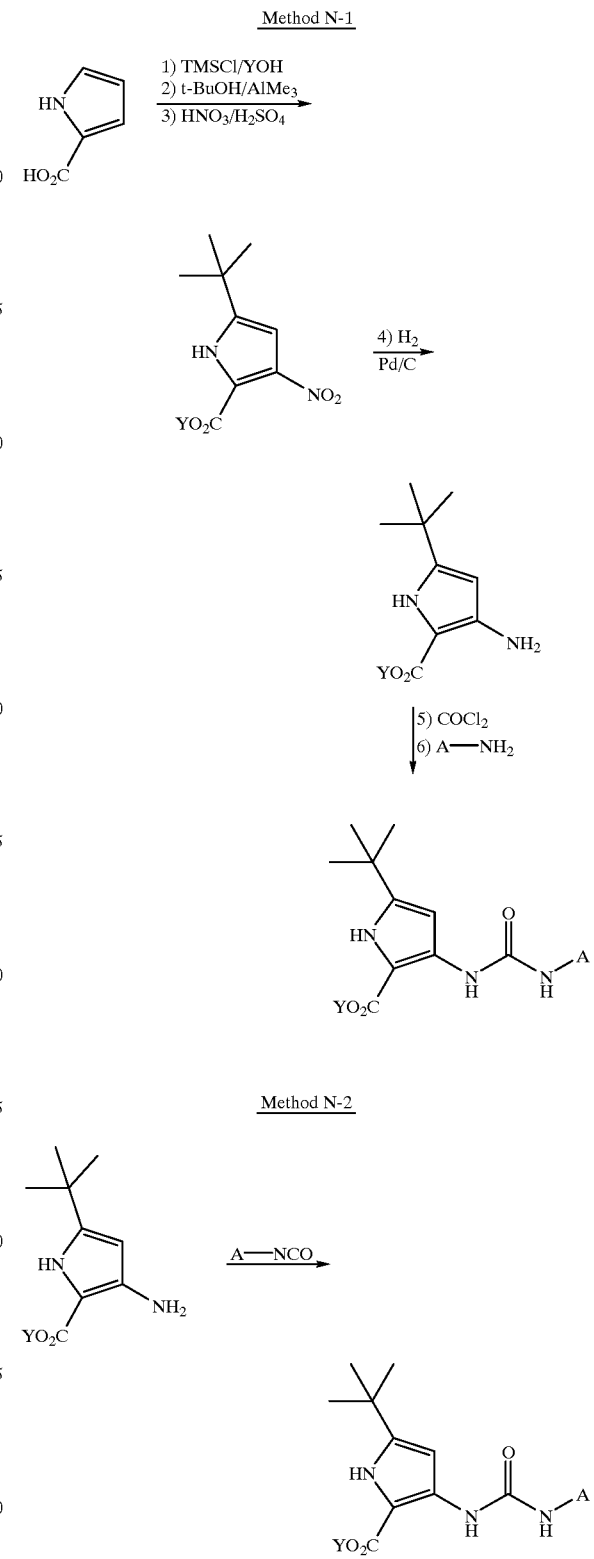

As shown in Method N-3, amide analogues of pyrroles may be generated by conversion of the 5-alkyl-3-nitropyrrole-2-carboxylic acid into the corresponding amide using standard coupling conditions (eg. 1-(3- dimethylaminopropyl)-3-ethylcarbodiimide, EDCI), followed by reduction of the nitro group and urea formation, as illustrated in Methods N-1 and N-2.

Method N-3

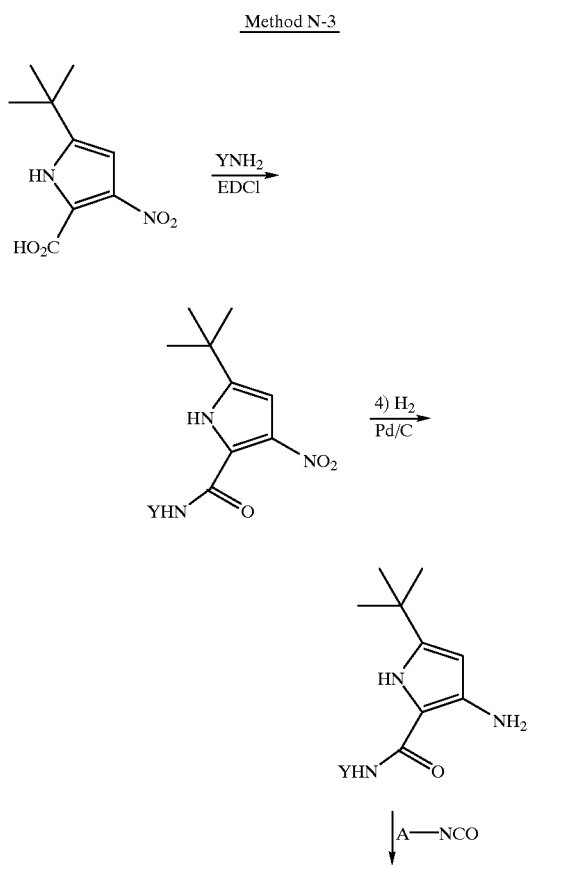

The 3-nitropyrrole generated in Method N-1 may also be treated with alkylating agents to form the N-alkyl-3-nitropyrrole (Method O). Reduction of the nitro moiety and urea formation proceed in a manner similar to that illustrated in Method N-1.

Method O

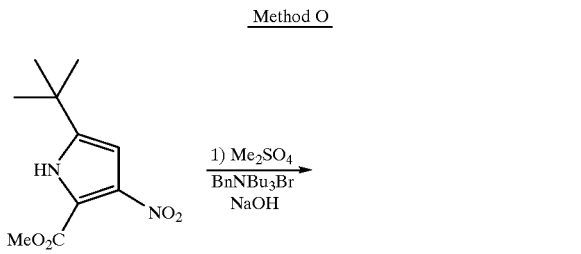

-continued

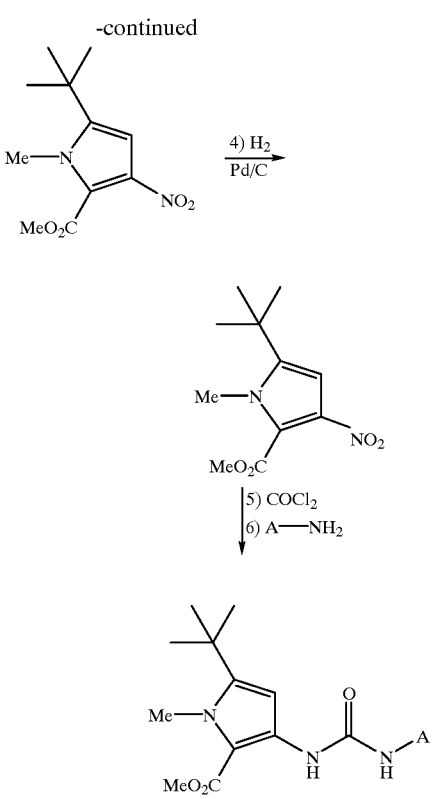

Methyl 5-tert-butyl-2-aminothiophene-3-carboxylates may be generated by the reaction of methyl cyanoacetate with 3,3-dimethylbutyraldehyde in the presence of elemental sulfur (Gewald et al. *Chem. Ber.* 1966, 99, 94; Method P). Urea formation may either involve treatment of the thus formed amine with an isocyanate, or an isocyanate equivalent (Method P), or the conversion of the amine into an isocyanate or an isocyanate equivalent by treatment with phosgene(Method Q) or a phosgene equivalent (Methods S and T), followed by reaction with a second amine.

Method P

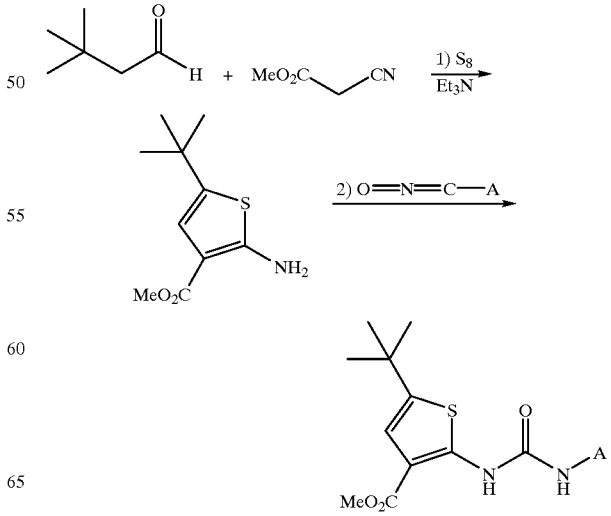

Method Q

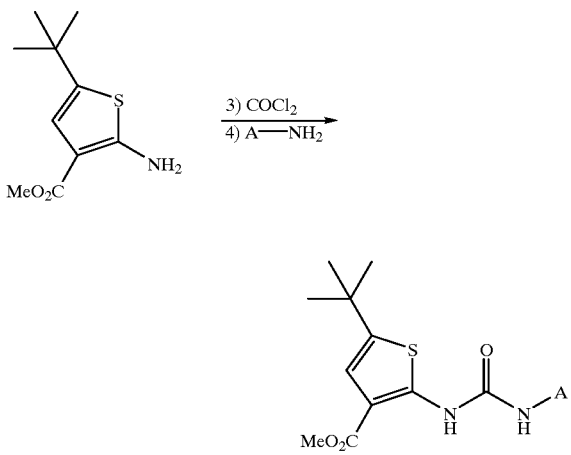

Methods S and T

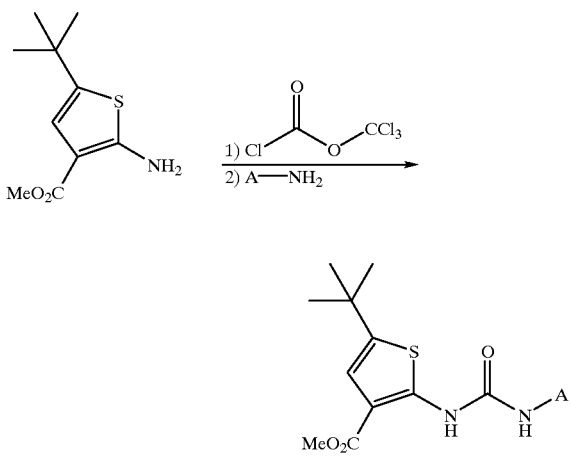

Similarly, formation of the 3-carbamoyl-2-thienylamine followed by treatment with an isocyanate affords the corresponding urea (Method U).

Method U

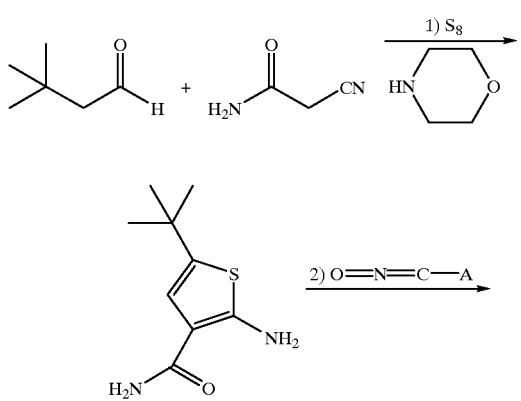

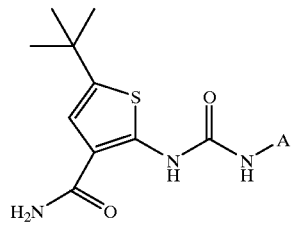

The invention also includes pharmaceutical compositions including a compound of Formulae I–V, and a physiologically acceptable carrier.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For all regimens of use disclosed herein for compounds of Formulae I–V, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily topical dosage regimen will preferably be from 0.1 to 200 mg administered between one to four times daily. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be appreciated by one skilled in the art that the specific dose level for a given patient depends on a variety of factors, including specific activity of the compound administered, age, body weight, health, sex, diet, time and route of administration, rate of excretion, etc. It will be further appreciated by one skilled in the art that the optimal course of treatment, ie, the mode of treatment and the daily number of doses of a compound of Formulae I–V or a pharmaceutically acceptable salt thereof given for a defined number of days, can be ascertained by those skilled in the art using conventional course of treatment tests.

The entire enclosure of all applications, patents and publications cited above and below are hereby incorporated by reference.

The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg. Bulb-to-bulb concentrations were conducted using an Aldrich Kugelrohr apparatus, and in these cases temperatures refer to oven temperatures.

All temperatures are reported uncorrected in degrees Celcius (° C.). Unless otherwise indicated, all parts and percentages are by volume.

Commercial grade reagents and solvents were used without further purification, except that tetrahydrofuran (THF) and 1,2-dimethoxyethane (DME) were doubly distilled from potassium, diethyl ether was distilled from sodium benzophenone ketyl, and $CH_2Cl_2$ was distilled from $CaH_2$.

Thin-layer chromatography (TLC) was performed on Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230–400 mesh EM Science® silica gel. Rotary chromatography was performed using pre-cast $SiO_2$ plates (Alltech®) on a Harrison Research Chromatotron.

Melting points (mp) were determined using a Thomas-Hoover melting point apparatus or a Mettler FP66 automated melting point apparatus and are uncorrected. Fourier transform infrared spectra were obtained using a Mattson 4020 Galaxy Series spectrophotometer. Proton ($^1H$) nuclear magnetic resonance (NMR) spectra were measured with a General Electric GN-Omega 300 (300 MHz) spectrometer with either $Me_4Si$ (d 0.00) or residual protonated solvent ($CHCl_3$ δ7.26; MeOH δ3.30; DMSO δ2.49) as standard. Carbon ($^{13}C$) NMR spectra were measured with a General Electric GN-Omega 300 (75 MHz) spectrometer with solvent ($CDCl_3$ δ77.0; MeOD-$d_3$; δ49.0; DMSO-$d_6$ δ39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer. Chemical ionization mass spectra (CI-MS) were obtained using a Hewlett Packard MS-Engine (5989A) with methane or ammonia as the reagent gas ($1\times10^{-4}$ torr to $2.5\times10^{-4}$ torr). The direct insertion desorption chemical ionization (DCI) probe (Vaccumetrics, Inc.) was ramped from 0–1.5 amps in 10 sec and held at 10 amps until all traces of the sample disappeared (~1–2 min). Spectra were scanned from 50–800 amu at 2 sec per scan. HPLC—electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120–800 amu using a variable ion time according to the number of ions in the source. Gas chromatography - ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses are conducted by Robertson Microlit Labs, Madison N.J.

All compounds displayed NMR spectra, LRMS and either elemental analysis or HRMS consistent with assigned structures.

List of Abbreviations and Acronyms

| AcOH | acetic acid |
| --- | --- |
| CI | chemical ionization |
| DMAP | 4-(N,N-dimethylamino)pyridine |
| DMF | N,N-dimethylformamide |
| DME | 1,2-dimethoxyethane |
| DMSO | dimethyl sulfoxide |
| EDCI | 1-(3-dimethylaminopropyl)-3-ethylcarbodiimide |
| EI | electron impact |
| $Et_3N$ | triethylamine |
| $Et_2O$ | diethyl ether |
| EtOAc | ethyl acetate |
| EtOH | ethanol |
| FAB | fast atom bombardment |
| GC-MS | gas chromatography mass spectrum |
| hex | n-hexane |
| FTIR | Fourier transform infrared |
| HPLC ES-MS | high pressure liquid chromatography electrospray mass spectrum |
| HRMS | high resolution mass spectrum |
| KOAc | potassium acetate |
| LRMS | low resoultion mass spectrum |
| MeOH | methanol |
| NaOMe | sodium methoxide |
| pet. ether | petroleum ether (boiling range 30–60° C.) |
| THF | tetrahydrofuran |
| $Ti(OEt)_4$ | tetraethoxytitanium(IV) |
| TMSCl | trimethylsilyl chloride |
| TLC | thin layer chromatography |
| $TMSCHN_2$ | (trimethylsilyl)diazomethane |

General Methods for the Synthesis of Urido Heterocycles
Method A
Synthesis of N-(2-carbomethoxy-5-isopropyl-3-thienyl)-N'-(phenyl)urea (Example 1).

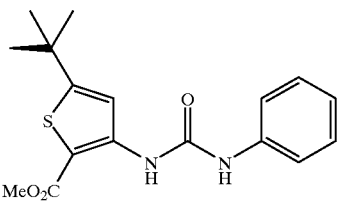

Step 1
To a solution of NaOMe (14 g) in MeOH (1 L) was added methyl thioglycolate (22.3 mL). The mixture was stirred for 5 min, then a solution of 3-chloro-4-methyl-2-pentenenitrile (32.4 g) in MeOH (200 mL) was added and the solution heated at the reflux temp. for 90 min. After cooling to 20° C., the mixture was concentrated under reduced pressure. The residue was dissolved in EtOAc, washed with a 1N HCl solution, dried ($MgSO_4$), and concentrated under reduced pressure. The residue was purified by flash chromatography (EtOAc/hexane) to yield methyl 3-amino-5-isopropylthiophene-2-carboxylate (8.0 g, 16%).
Step 2
To a solution of methyl 3-amino-5-isopropylthiophene-2-carboxylate (0.050 g, 0.25 mmol) in toluene (1 mL) was added phenyl isocyanate (0.024 mL, 0.25 mmol, 1.0 equiv) and the resulting mixture was heated at the reflux temp. for 6 h, then cooled to 20° C. during which N-(2-carbomethoxy-5-isopropyl-3-thienyl)-N'-(phenyl)urea crystallized from solution (0.014 g, 18%): mp 108–10° C.; $^1$H NMR ($CDCl_3$) δ1.3 (d, 6H), 3.1 (m, 1H), 3.8 (s, 3H), 6.7 (br s, 1H), 7.2 (m, 1H), 7.3 (m, 3H), 7.83 (s, 1H); EI-LRMS m/z 318 ($M^+$).
Selected Compound Synthesized Using Method A
N-(2-Carbomethoxy-5-tert-butyl-3-thienyl)-N'-(4-methylphenyl)urea (Example 5): mp 124–6° C.; $^1$H NMR ($CDCl_3$) δ1.34 (s, 9H), 2.30 (s, 3H), 3.76 (s, 3H), 7.12 (d, J=8.5 Hz, 2H), 7.29 (d, J=8.5 Hz, 2H), 7.48 (br s, 1H), 7.87 (s, 1H), 9.67 (s, 1H); $^{13}$C NMR ($CDCl_3$) δ20.8, 31.7 (3C), 35.2, 51.6, 104.9, 117.2, 121.4 (2C), 129.7 (2C), 134.0, 135.1, 145.9, 152.2, 164.4, 165.0.
Method B
Synthesis of N-(2-carbomethoxy-5-tert-butyl-3-thienyl)-N'-(4-fluorophenyl)urea (Example 54).

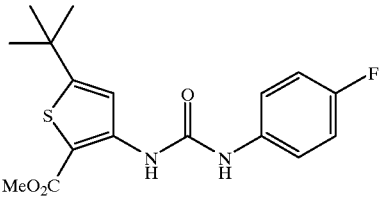

Step 1
To a solution of phosgene (1.93M in toluene, 7.9 mL, 15.2 mmol, 3.0 equiv) in $CH_2Cl_2$ (100 mL) at 0° C. was added a solution of methyl 3-amino-5-tert-butylthiophene-2-carboxylate (1.08 g, 5.07 mmol) and pyridine (1.6 mL, 20.3 mmol, 4.0 equiv) in $CH_2Cl_2$ (30 mL). The reaction mixture was allowed to slowly warm to room temp. and was stirred at that temp. for 30 min. The resulting slurry was concentrated under reduced pressure to give a mixture of 2-carbomethoxy-5-tert-butyl-3-thienyl isocyanate and pyridinium hydrochloride as a yellow solid. 2-Carbomethoxy-5-tert-butyl-3-thienyl isocyanate: $^1$H NMR (CDCl$_3$) δ1.36 (s, 9H), 3.89 (s, 3H), 6.55 (s, 1H). The mixture was used in the next step without further purification.

Step 2

The 2-carbomethoxy-5-tert-butyl-3-thienyl isocyanate prepared in Method B, Step 1 was dissolved in anh. THF (100 mL). 4-Fluoroaniline (1.13 g, 10.1 mmol, 2.0 equiv) was added and the resulting solution was stirred at room temp. for 14 h. The resulting mixture was diluted with CHCl$_3$ (200 mL) then washed with a 1N HCl solution (2×100 mL) and a saturated NaCl solution (100 mL). The combined aqueous layers were back-extracted with CHCl$_3$ (100 mL). The combined organic layers were dried (Na$_2$SO$_4$) and concentrated under reduced pressure to give a yellow-brown solid (1.61 g), which was recrystallized (CH$_2$Cl$_2$) to give N-(2-carbomethoxy-5-tert-butyl-3-thienyl)-N'-(4-fluorophenyl)urea as a white solid (1.34 g, 75% over 2 steps): mp 160–2° C.; TLC (20% EtOAc/hexane) R$_f$0.45; $^1$H NMR (CDCl$_3$) δ1.33 (s, 9H), 3.77 (s, 3H), 7.01 (dd, J=8.8, 8.5 Hz, 2H), 7.34–7.39 (m, 2H), 7.49 (s, 1H), 7.82 (s, 1H), 9.68 (s, 1H); $^{13}$C NMR (CDCl$_3$) δ31.7 (3C), 35.2, 51.6, 105.1, 115.9 (d, J$_{C-F}$=22.0 Hz, 2C), 117.1, 123.2 (d, J$_{C-F}$=7.3 Hz, 2C), 133.7 (d, J$_{C-F}$=2.4 Hz, 1C), 145.8, 148.6, 152.2, 159.6 (d, J$_{C-F}$=244.1 Hz, 1C), 164.7, 165.1; FAB-LRMS m/z (rel abundance) 351 (M+H, 33%).

Selected Compounds Synthesized Using Method B

N-(2-Carbomethoxy-5-tert-butyl-3-thienyl)-N'-(3-methylphenyl)urea (Example 9): mp 70–2° C.; $^1$H NMR (CDCl$_3$) δ1.4 (s, 9H), 2.4 (s, 3H), 3.8 (s, 3H), 6.75 (br s, 1H), 6.95 (d, 1H), 7.2–7.3 (m, 3H), 7.8 (s, 1H), 9.7 (s, 1H); FAB-LRMS m/z (rel abundance) 347 (M+H, 56%).

N-(2-Carbomethoxy-5-tert-butyl-3-thienyl)-N'-(5-cyclopropyl-2-thiadiazolyl)urea (Example 16): $^1$H NMR (CDCl$_3$) δ1.20–1.40 (m, 4H), 1.40 (s, 9H), 2.25–2.35 (m, 1H), 3.80 (s, 3H), 7.75 (s, 1H), 10.00 s, 1H); FAB-LRMS m/z (rel abundance) 381 (M+H, 18%).

Method C

Synthesis of N-(2-carbomethoxy-5-tert-butyl-3-thienyl)-N'-(2-aminophenyl)urea (Example 11).

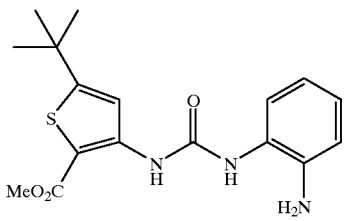

N-(2-Carbomethoxy-5-tert-butyl-3-thienyl)-N'-(2-nitrophenyl)urea was synthesized in a manner analogous to that described in Method B.

A slurry of N-(2-carbomethoxy-5-tert-butyl-3-thienyl)-N'-(2-nitrophenyl)urea (0.078 g, 0.21 mmol) and 10% Pd/C (0.010 g) in MeOH (15 mL) was stirred under H$_2$ (1 atm.) for 18 h at 20° C. Celite® was added and the slurry was filtered. The resulting solution was concentrated under reduced pressure and the residue was purified by flash chromatography (gradient from 20% EtOAc/hexane to 50% EtOAc/hexane) to afford N-(2-carbomethoxy-5-tert-butyl-3-thienyl)-N'-(2-aminophenyl)urea as a foam (0.060 g, 83%): $^1$H NMR (CDCl$_3$, partial spectrum) δ1.4 (s, 9H), 3.6 (s, 3H), 6.8–7.3 (m, 4H), 7.8 (s, 1H), 9.6 (s, 1H); FAB-LRMS m/z (rel abundance) 348 (M+H, 34%).

Method D

Synthesis of N-(2-carboethoxy-5-tert-butyl-3-thienyl)-N'-(4-methylphenyl)urea (Example 6).

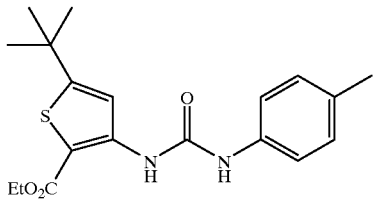

A solution of Ti(OEt)$_4$ (0.10 mL, 0.476 mmol, 11.8 equiv), N-(2-carbomethoxy-5-tert-butyl-3-thienyl)-N'-(4-methylphenyl)urea (0.014 g, 0.040 mmol), and EtOH (10 mL) was heated at the reflux temp. for 36 h. The resulting mixture was filtered and the filtrate was concentrated under reduced pressure. The residual oil was dissolved in EtOAc and purified by flash chromatography (gradient from 10% EtOAc/hexane to 20% EtOAc/hexane) to afford N-(2-carboethoxy-5-tert-butyl-3-thienyl)-N'-(4-methylphenyl)urea (0.0086 g, 59%): $^1$H NMR (CDCl$_3$) δ1.30 (d, J=7.4 Hz, 3H), 1.35 (s, 9H), 2.30 (s, 3H), 4.24 (q, J=7.4 Hz, 2H), 7.11 (d, J=8.5 Hz, 2H), 7.29 (d, J=8.5 Hz, 2H), 7.30 (br s, 1H), 7.86 (s, 1H), 9.68 (s, 1H); $^{13}$C NMR (CDCl$_3$) δ14.3, 20.8, 31.8 (3C), 35.2, 60.6, 105.1, 117.2, 121.0 (2C), 129.7 (2C), 133.8, 135.2, 145.9, 152.1, 164.2, 164.8.

Method E

Synthesis of N-(2-(carbo-1-prop-2-enyloxy)-5-tert-butyl-3-thienyl)-N'-(4-methylphenyl)urea (Example 8).

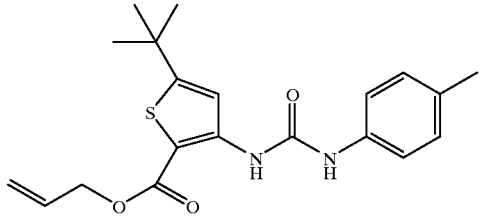

Step 1

To a solution of methyl 3-amino-5-tert-butylthiophene-2-carboxylate (10.0 g, 47 mmol) and DMAP (6.57 g, 47 mmol, 1.0 equiv) in pyridine (188 mL) at 0° C. was added di-tert-butyl dicarbonate (11.3 g, 51.7 mmol, 1.1 equiv). The pyridine solution was allowed to warm to room temp. and was stirred for 6 d. The resulting mixture was concentrated under reduced pressure to yield an orange solid, which was separated between CH$_2$Cl$_2$ (250 mL) and a 1M H$_3$PO$_4$ solution (100 mL). The organic phase was washed with a saturated NaHCO$_3$ solution (100 mL) and a saturated NaCl solution (100 mL), dried (MgSO$_4$) and concentrated under reduced pressure. The resulting light orange solid was recrystallized (EtOH/H$_2$O) to give methyl 3-(N-carbo-tert-butoxyamino)-5-tert-butylthiophene-2-carboxylate as an off-white solid (12.00 g, 82%): TLC (10% EtOAc) R$_f$0.65; $^1$H NMR (CDCl$_3$) δ1.38 (s, 9H), 1.51 (s, 9H), 3.84 (s, 3H), 7.68 (s, 1H) 9.35 (s, 1H); $^{13}$C NMR (CDCl$_3$) δ28.6 (3C), 32.0 (3C), 35.4, 51.8, 81.1, 105.2, 116.6, 145.7, 152.4, 164.5, 165.0.

Step 2

To a solution of methyl 3-(N-carbo-tert-butoxyamino)-5-tert-butylthiophene-2-carboxylate (10.7 g, 34.1 mmol) in a 2:1:1 mixture of THF, MeOH and H$_2$O (340 mL) was added NaOH (4.09 g, 102.3 mmol, 3.0 equiv). The resulting solution was heated at 60° C. for 18 h, cooled to room temp. and concentrated under reduced pressure. The residue was separated between H$_2$O (500 mL) and EtOAc (250 mL). The aqueous phase was adjusted to pH 2 with a 10% HCl solution, then extracted with EtOAc (2×400 mL). The organic phase was washed with a saturated NaCl solution (250 mL), dried (MgSO$_4$), and concentrated under reduced pressure to afford 3-(N-carbo-tert-butoxyamino)-5-tert-butylthiophene-2-carboxylic acid as an orange solid (6.6 g, 65%). This material was used in the next step without further purification. An analytical sample of the carboxylic acid was further purified: mp 187–8° C., TLC (10% MeOH/CH$_2$Cl$_2$) R$_f$0.17; $^1$H NMR (CDCl$_3$) δ1.40 (s, 9H), 1.54 (s, 9H), 7.73 (s, 1H), 9.19 (s, 1H); $^{13}$C NMR (CDCl$_3$) δ28.2 (3C), 31.8 (3C), 35.4, 81.3, 104.6, 116.7, 146.7, 151.9, 166.6, 169.3; FAB-LRMS m/z (rel abundance) 300 (M+H, 30%).

Step 3

To a solution of 3-(N-carbo-tert-butoxyamino)-5-tert-butylthiophene-2-carboxylic acid (0.20 g, 0.67 mmol), allyl alcohol (0.042 g, 0.73 mmol, 1.1 equiv) and DMAP (0.008 g, 0.07 mmol, 10 mol %) in CH$_2$Cl$_2$ (2 mL) was added EDCI.HCl (0.14 g, 0.73 mmol, 1.1 equiv). The CH$_2$Cl$_2$ mixture was stirred at room temp. for 3 d, diluted with CH$_2$Cl$_2$, washed with a 1N HCl solution (5 mL) and a saturated NaHCO$_3$ solution (5 mL), dried (Na$_2$SO$_4$), and concentrated under reduced pressure to afford allyl 3-(N-carbo-tert-butoxyamino)-5-tert-butylthiophene-2-carboxylate (0.15 g, 65%) as a colorless oil: TLC (50% CH$_2$Cl$_2$/hexane) R$_f$0.63; $^1$H NMR (CDCl$_3$) δ1.37 (s, 9H), 1.50 (s, 9H), 4.74 (ddd, J=5.5, 1.5, 1.5 Hz, 2H), 5.26 (dd, J=10.3, 1.5 Hz, 1H), 5.37 (dd, J=17.3, 1.5 Hz, 1H), 5.87–5.98 (m, 1H), 7.68, 9.35; $^{13}$C NMR (CDCl$_3$) δ28.2 (3C), 31.8 (3C), 35.2, 64.9, 80.8, 104.9, 116.4, 118.1, 132.0, 145.6, 152.1, 164.0, 164.4

Step 4

Allyl 3-(N-carbo-tert-butoxyamino)-5-tert-butylthiophene-2-carboxylate (0.14 g, 0.41 mmol) was dissolved in solution of HCl in dioxane (4N, 11.0 mL, 4.1 mmol, 10 equiv). The resulting solution was stirred at room temp. for 5 d, diluted with CHCl, (5 mL), washed with a 1N HCl solution (5 mL) and a saturated NaCl solution (5 mL), dried Na$_2$SO$_4$), and concentrated under reduced pressure. The residue was filtered through a plug of SiO$_2$ with the aid of a 10% EtOAc/CH$_2$Cl$_2$ solution to give allyl 3-amino-5-tert-butylthiophene-2-carboxylate as a yellow oil (0.088 g, 95%): $^1$H NMR (CDCl$_3$) δ1.32 (s, 9H), 4.72 (ddd, J=4.1, 1.5, 1.5 Hz, 2H), 5.21 (ddd, J=10.3, 2.9, 1.5 Hz, 1H), 5.36 (ddd, J=17.3, 3.1, 1.5, 1H), 5.42 (br s, 2H), 5.92–6.03 (m, 1H), 6.34 (s, 1H). This material was used without further purification.

Step 5

To a solution of allyl 3-amino-5-tert-butylthiophene-2-carboxylate (0.088 g, 0.39 mmol) and pyridine (0.12 g, 1.56 mmol, 4.0 equiv) in CH$_2$Cl$_2$ (4 mL) at 0° C. was added a solution of phosgene in toluene (1.93M, 0.6 mL, 1.17 mmol, 3.0 equiv). The reaction was allowed to slowly warm to room temp. and stirred for 2 h. The resulting mixture was concentrated under reduced pressure. The residue was dissolved in anh. THF (4 mL), 4-methylaniline (0.083 g, 0.78 mmol, 2.0 equiv) was added, and the resulting solution was stirred at room temp. for 14 h. The THF mixture was diluted with CHCl$_3$ (10 mL) and the resulting solution was washed with a 1N HCl solution (10 mL) and concentrated under reduced pressure. The residue was purified by flash chromatography (gradient from hexane to 10% EtOAc/hexane) to give N-(2-carbo-1-prop-2-enyloxy-5-tert-butyl-3-thienyl)-N'-(4-methylphenyl)urea as a white solid (0.087 g, 60%): mp 52–62° C., TLC (10% EtOAc/hexane) R$_f$0.34; $^1$H NMR (CDCl$_3$) δ1.36 (s, 9H), 2.32 (s, 3H), 4.69 (app dt, J=5.5, 1.5 Hz, 2H), 5.25 (dd, J=10.3, 1.5 Hz, 1H), 5.35 (dd, J=16.9, 1.5 Hz, 1H), 5.87–5.98 (m, 1H), 7.13 (d, J=8.0 Hz, 2H), 7.30 (d, J=8.5 Hz, 2H), 7.88 (s, 1H), 9.68 (s, 1H); $^{13}$C NMR (CDCl$_3$) δ20.8, 31.7 (3C), 35.2, 65.0, 104.9, 117.2, 118.2, 121.3 (2C), 129.7 (2C), 131.9, 134.0, 135.0, 146.1, 151.2, 164.3, 165.6; FAB-LRMS m/z (rel abundance) 373 (M+H, 13%).

Selected Compounds Synthesized Using Method E

N-(2-(Carbo-2-propyloxy)-5-tert-butyl-3-thienyl)-N'-(4-methylphenyl)urea (Example 7): mp 72–86° C., TLC (10% EtOAc/hexane) R$_f$0.34; $^1$H NMR (CDCl$_3$) δ1.28 (d, J=6.3 Hz, 3H), 1.35 (s, 9H), 2.31 (s, 3H), 5.11 (sept, J=6.3 Hz, 1H), 7.11 (d, J=8.1 Hz, 2H), 7.28 (d, J=8.1 Hz, 2H), 7.85 (s, 1H), 9.76 (s, 1H); $^{13}$C NMR (CDCl$_3$) δ20.8, 21.9 (2C), 31.8 (3C), 35.2, 68.2, 105.6, 117.2, 121.2 (2C), 129.7 (2C), 133.8, 135.1, 145.7, 152.1, 163.9, 164.4; FAB-LRMS m/z (rel abundance) 375 (M+H, 70%).

N-(2-(Carbo-1-propyloxy)-5-tert-butyl-3-thienyl)-N'-(4-methylphenyl)urea (Example 53): mp 59–66° C., TLC (10% EtOAc/hexane) R$_f$38; $^1$H NMR (CDCl$_3$) δ0.96 (t, J=7.5 Hz, 3H), 1.35 (s, 9H), 1.69 (app hex, J=7.4 Hz, 2H), 2.31 (s, 3H), 4.14 (t, J=6.8 Hz, 2H), 7.11 (d, J=8.1 Hz, 2H), 7.29 (d, J=8.5 Hz, 2H), 7.86 (s, 1H), 9.71 (s, 1H); $^{13}$C NMR (CDCl$_3$) δ10.3, 20.8, 22.0, 31.7 (3C), 35.2, 66.1, 105.3, 117.2, 121.2 (2C), 129.7 (2C), 133.9, 135.0, 145.7, 152.1, 164.2, 164.8; FAB-LRMS m/z (rel abundance) 375 (M+H, 36%).

Method F

Synthesis of N-(2-methylcarbamoyl-5-tert-butyl-3-thienyl)-N'-(4-methylphenyl)urea (Example 22).

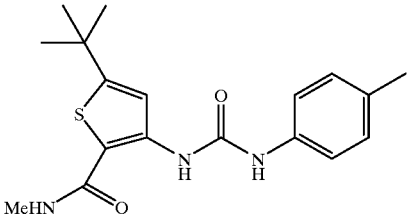

Step 1

A solution of methyl 3-amino-5-tert-butylthiophene-2-carboxylate (20.0 g, 93.9 mmol), benzyl chloroformate (80.4 mL, 563 mmol), Na$_2$CO$_3$ (1.10 g, 9.93 mmol), toluene (400 mL) and water (50 mL) was heated at the reflux temp. for 18 h. Volatiles were removed under reduced pressure. The resulting oil was dissolved in EtOAc, washed with water and a concentrated NaCl solution, dried (MgSO$_4$) and concentrated under reduced pressure to afford methyl 3-(N-carbobenzyloxyamino)-5-tert-butylthiophene-2-carboxylate as a crude oil in quantitative yield.

Step 2

To a saturated solution of methylamine in MeOH (200 mL) in a screw top vessel was added methyl 3-(N-carbobenzyloxyamino)-5-tert-butylthiophene-2-carboxylate (13.6 g, 39.2 mmol) and NaCN (0.98 g, 20 mmol). The vessel was sealed and the reaction mixture was heated to 50° C. for 8 h. The resulting solution was poured into water (500 mL) and extracted with EtOAc. The organic layer was washed with water and a concentrated NaCl solution, dried (Na$_2$SO$_4$), and concentrated under reduced pressure. The crude material was purified by flash chromatography (EtOAc/hexane) affording N-methyl-3-(N-carbobenzyloxyamino)-5-tert-butylthiophene-2-carboxamide (2.76 g, 20%).

Step 3

N-Methyl-3-(N-carbobenzyloxyamino)-5-tert-butylthiophene-2-carboxamide (2.76 g, 8 mmol) was dissolved in a 1:1 v/v solution of 48% HBr and AcOH (100 mL) and heated to 30° C. for 24 h. The acidic solution was cooled and adjusted to pH 4 with a saturated NaHCO$_3$ solution. Methylamine (4 mL, 2M in THF) was added and the resulting mixture was extracted with CH$_2$Cl$_2$. The organic phase was concentrated under reduced pressure to afford N-methyl-3-amino-5-tert-butylthienyl-2-carboxamide (0.092 g, 54%).

Step 4

A solution of the N-methyl-3-amino-5-tert-butylthiophene-2-carboxamide (0.60 g, 2.83 mmol) and 4-methylphenyl isocyanate (0.36 mL, 2.83 mmol) in toluene (2 mL) was heated at the reflux temp. for 18 h. The resulting solution was concentrated under reduced pressure and the resulting solid was purified by flash chromatography (EtOAc/CH$_2$Cl$_2$) affording N-(2-methylcarbamoyl-5-tert-butyl-3-thienyl)-N'-(4-methylphenyl)urea (0.42 g, 44%): mp 202–4° C.; $^1$H NMR (CDCl$_3$) δ1.38 (s, 9H), 2.31 (s, 3H), 2.91 (d, J=4.9 Hz, 3H), 5.59 (bs, 1H), 7.11 (d, J=8.5 Hz, 2H), 7.29 (d, J=8.5 Hz, 2H), 7.90 (s, 1H), 10.53 (s, 1H).

Method G

Synthesis of N-(2-methylcarbamoyl-5-tert-butyl-3-thienyl)-N'-(4-fluorophenyl)urea (Example 25).

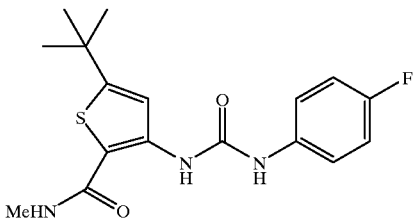

Step 1

A slurry of methylamine hydrochloride (9.51 g, 141 mmol, 3.1 equiv) in anh. toluene (600 mL) at 0° C. was treated with AlMe$_3$ (2M in toluene, 70 mL, 141 mmol, 3.1 equiv) over 10 min. The resulting solution was stirred at 0° C. for 1 h then allowed to warm to room temp. and stirred for 40 min. Methyl 3-amino-5-tert-butylthiophene-2-carboxylate (9.87 g, 46 mmol) was added to the aluminum amide solution. The resulting mixture was heated at the reflux temp. for 3 d, cooled to 0° C., and a 6N HCl solution was added dropwise. The quenched mixture was made basic with a 20% KOH solution (95 mL). The resulting slurry was partitioned between H$_2$O (300 mL) and EtOAc (300 mL) and the aqueous layer was extracted with EtOAc (3×300 mL). The combined organic layers were dried (Na$_2$SO$_4$) and concentrated under reduced pressure to afford N-methyl-3-amino-5-tert-butylthiophene-2-carboxamide as a green-yellow solid (9.47 g, 97%): mp 230–1° C.; TLC (20% EtOAc/CH$_2$Cl$_2$) R$_f$0.23; $^1$H NMR (d$^6$-DMSO) δ1.28 (s, 9H), 2.63 (d, J=4.8 Hz, 3H), 6.29 (br s, 2H), 6.37 (d, J=1.1 Hz, 1H), 7.22 (q, J=4.0 Hz, 1H).

Step 2

A slurry of N-methyl-3-amino-5-tert-butylthiophene-2carboxamide (7.63 g, 36 mmol) and 4-fluorophenyl isocyanate (4.93 g, 36 mmol, 1.0 equiv) in anh. toluene (100 mL) was heated at the reflux temp. for 3 h, during which the mixture clarified then generated a new precipitate, which was filtered while hot. The resulting solids were washed with hexane and dried under reduced pressure to afford N-(2-methylcarbamoyl-5-tert-butylthienyl)-N'-(4-fluorophenyl)urea (10.2 g, 81%): mp 203–4° C.; TLC (5% MeOH/CH$_2$Cl$_2$) R$_f$0.61; $^1$H NMR (CDCl$_3$) δ1.34 (s, 9H), 2.73 (d, J=4.4 Hz, 3H), 7.07–7.13 (m, 2H), 7.49–7.54 (m, 2H), 7.80 (s, 1H), 7.96 (q, J=4.4 Hz, 1H), 9.88 (s, 1H), 10.46 (s, 1H); $^{13}$C NMR (CDCl$_3$) δ25.8, 31.6 (3C), 34.5, 107.4, 115.2 (d, J$_{C-F}$=22.0 Hz, 2C), 117.3, 120.1 (d, J$_{C-F}$=7.3 Hz, 2C), 136.1 (d, J$_{C-F}$=2.4 Hz, 2C), 143.1, 151.6, 157.4 (d, J$_{C-F}$=238.1 Hz, 1C), 158.0, 164.3; EI-LRMS m/z (rel abundance) 349 (M$^+$, 13%).

Selected Compounds Synthesized Using Method G

N-(2-Methylcarbamoyl-5-tert-butyl-3-thienyl)-N'-(4ethylphenyl)urea (Example 23): mp 101–4° C., TLC (20% EtOAc.hexane) R$_f$0.18; $^1$H NMR (CDCl$_3$) δ1.20 (t, J=7.7 Hz, 3H), 1.20 (s, 9H), 2.59 (q, J=7.7 Hz, 2H), 2.88 (d, J=4.8 Hz, 3H), 5.64 (br d, J=4.4 Hz, 1H), 7.12 (d, J=8.1 Hz, 2H), 7.32 (d, J=8.5 Hz, 2H), 7.42 (br m, 1H), 7.90 (s, 1H), 10.54 (s, 1H); $^{13}$C NMR (CDCl$_3$) δ15.6, 26.3, 28.2, 31.8 (3C), 35.0, 106.8, 118.1, 120.2 (2C), 128.3 (2C), 135.9, 139.5, 144.5, 152.1, 159.5, 165.6; FAB-LRMS m/z (rel abundance) 360 (M+H, 14%).

N-(2-Methylcarbamoyl-5-tert-butyl-3-thienyl)-N'-(4-isopropylphenyl)urea (Example 24): mp 113–20° C., TLC (20% EtOAc.hexane) R$_f$0.20; $^1$H NMR (d$^6$-DMSO) δ1.17 (d, J=7.0 Hz, 6H), 1.35 (s, 9H), 2.73 (d, J=4.4 Hz, 3H), 2.82 (sept, J=7.0 Hz, 1H), 7.13 (d, J=8.5 Hz, 2H), 7.41 (d, J=8.1 Hz, 2H), 7.80 (s, 1H), 7.93 (br q, J=4.8 Hz, 1H), 9.75 (s, 1H), 10.40 (s, 1H); $^{13}$C NMR (CDCl$_3$) δ15.8 (2C), 25.9, 27.5, 31.6 (3C), 34.5, 107.3, 118.5 (2C), 127.8 (2C), 137.2, 137.5, 143.2, 151.6, 157.9, 164.3; FAB-LRMS m/z (rel abundance) 374 (M+H, 50%).

N-(2-Methylcarbamoyl-5-tert-butyl-3-thienyl)-N'-(2,4-dimethylphenyl)urea (Example 27): mp 195–6° C.; $^1$H NMR (d$^6$-DMSO) δ1.32 (s, 9H), 2.17 (s, 3H), 2.23 (s, 3H), 2.71 (d, J=4.4 Hz, 3H), 6.93 (br d, J=8.1 Hz, 1H), 6.98 (br s, 1H), 7.27 (d, J=8.1 Hz, 1H), 7.89 (q, J=4.0 Hz, 1H), 8.96 (s, 1H), 10.31 (s, 1H); EI-LRMS m/z (rel abundance) 359 (M$^+$, 7%).

N-(2-Methylcarbamoyl-5-tert-butyl-3-thienyl)-N'-(3-chloro-4-methylphenyl)urea (Example 28): mp 178–9° C.; $^1$H NMR (d$^6$-DMSO) δ1.31 (s, 9H), 2.24 (s, 3H), 2.72 (d, J=4.4 Hz, 3H), 7.19–7.24 (m, 2H), 7.73 (d, J=1.8 Hz, 1H), 7.79 (s, 1H), 7.97 (br q, J=4.3 Hz, 1H), 9.96 (s, 1H), 10.49 (s, 1H); EI-LRMS m/z (rel abundance) 379 (M$^+$, 30%), 381 (M$^+$+2, 14%).

N-(2-Methylcarbamoyl-5-tert-butyl-3-thienyl)-N'-(3-fluoro4-methylphenyl)urea (Example 29): mp 182–3° C; $^1$H NMR (d$^6$-DMSO) δ1.32 (s, 9H), 2.13 (d, J$_{F-H}$=1.5 Hz, 3H), 2.70 (d, J=4.4 Hz, 3H), 7.08–7.12 (m, 2H), 7.42 (dd, J=1.8, 12.5 Hz, 2H) 7.76 (s, 1H), 7.95 (q, J=4.8 Hz, 1H), 9.94 (s, 1H), 10.45 (s, 1H); FAB-LRMS m/z (rel abundance) 364 (M+H, 10%).

N-(2-Methylcarbamoyl-5-tert-butyl-3-thienyl)-N'-(3chloro-4-fluorophenyl)urea (Example 30): mp 203–4° C.; $^1$H NMR (d$^6$-DMSO) δ1.34 (s, 9H), 2.72 (d, J=4.4 Hz, 3H), 7.31–7.35 (m, 2H), 7.77 (s, 1H), 7.84 (dm, J=5.9 Hz, 1H), 7.99 br q, J=4.4 Hz, 1H), 10.06 (s, 1H), 10.54 (s, 1H); FAB-LRMS m/z (rel abundance) 359 (M+H, 52%), 386 (M+2+H, 22%).

Method H
Synthesis of N-(2-carboxy-5-tert-butyl-3-thienyl)-N'-(4-methylphenyl)urea (Example 4).

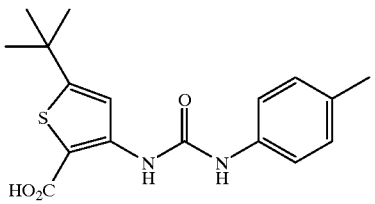

N-(2-Carbobenzyloxy-5-tert-butyl-3-thienyl)-N'-(4-methylphenyl)urea was synthesized as described in Method E.

To a solution of N-(2-carbobenzyloxy-5-tert-butyl-3-thienyl)-N'-(4-methylphenyl)urea (0.19 g, 0.40 mmol) in EtOH (19 mL) was added 10% Pd/C (0.010 g). The resulting suspension was treated with $H_2$ (52 psi) in a Parr® shaker for 18 h. The slurry was filtered through a pad of Celite® and concentrated under reduced pressure to afford N-(2-carboxy-5-tert-butyl-3-thienyl)-N'-(4-methylphenyl)urea (0.12 g, 90%): $^1$H NMR ($d^6$-DMSO) δ13 (s, 9H), 2.2 (s, 3H), 7.1 (d, 2H), 7.4 (d, 2H), 7.8 (s, 1H); FAB-LRMS m/z) 333 (M+H).

Method I
Synthesis of N-(2-(N-glycylaminomethyl)-5-tert-butyl-3-thienyl)-N'-(4-methylphenyl)urea (Example 51).

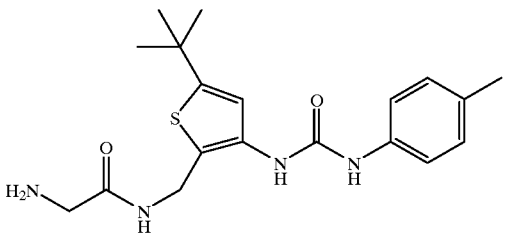

Step 1
N2-Carbamoyl-5-tert-butyl-3-thienyl)-N'-(4-methylphenyl)urea was synthesized in a manner analogous to that described in Method F.

To a solution of $BH_3$THF (1.8 mL, 1M in THF) was added a solution of N-(2-carbamoyl-5-tert-butyl-3-thienyl)-N'-(4-methylphenyl)urea in THF (3 mL) and the resulting mixture was heated under reflux for 48 h. After cooling to room temp., a concentrated hydrochloric acid solution was added, and the resulting mixture was extracted with EtOAc. The organic layer was washed with a saturated $Na_2CO_3$ solution, and a saturated NaCl solution, dried ($MgSO_4$), and concentrated under reduced pressure. The residue was purified by chromatography ($SiO_2$, 0.1% $NH_4OH$/10% MeOH/$CH_2Cl_2$ to afford N-(2-aminomethyl-5-tert-butyl-3-thienyl)-N'-(4-methylphenyl)urea (0.18 g, 85%): $^1$H NMR ($CDCl_3$) δ1.38 (s, 9H), 2.34 (s, 3H), 3.81 (s, 2H), 6.72 (s, 1H), 7.29 (d, J=8.6 Hz, 2H), 7.16 (d, J=8.5 Hz, 2H), 7.87 (s, 1 h); FAB-LRMS m/z 318 (M+H).

Step 2
To a solution of N-(2-aminomethyl-5-tert-butyl-3-thienyl)-N'-(4-methylphenyl)urea (0.20 g, 0.63 mmol) and N-carbo-tert-butoxyglycine (0.11 g, 0.63 mmol, 1.0 equiv) in THF (2 mL) at room temp. were added dicyclohexylcarbodiimide (0.13 g, 0.63 mmol, 1.0 equiv) and 1-hydroxybenzotriazole monohydrate (0.008 g, 0.06 mmol, 10 mol %). The resulting mixture was allowed to stir 18 h, diluted with EtOAc (5 mL), and washed with a saturated NaCl solution. The organic layer was dried ($MgSO_4$) and concentrated under reduced pressure. The residue was purified by flash chromatography (gradient from 30% EtOAc/hexane to 50% EtOAc/hexane) to afford N-(2-(N-(N-carbo-tert-butoxyglycyl)aminomethyl)-5-tert-butyl-3-thienyl)-N'-(4-methylphenyl)urea (0.12 g, 40%, Example 52): mp 174–176° C.; $^1$H NMR ($CDCl_3$) δ1.38 (s, 9H), 2.27 (m, 3H), 4.38 (m, 2H), 6.67 (bs, 1H), 6.89 (m, 1H), 7.27 (m, 1H), 7.33 (m, 2H), 8.58 (bs, 1H); FAB-LRMS m/z 475 (M+H).

Step 3
To a solution of N-(2-(N-(N-carbo-tert-butoxyglycyl)aminomethyl)-5-tert-butyl-3-thienyl)-N'-(4-methylphenyl)urea (0.050 g, 0.105 mmol) in $CH_2Cl_2$ (3 mL) at room temp. was added trifluoroacetic acid (0.50 mL, 6.49 mmol, 62 equiv). The resulting mixture was stirred for 3 h, washed with a saturated $NaHCO_3$ solution, dried ($MgSO_4$), and concentrated under reduced pressure. The residue was purified by flash chromatography (for $CH_2Cl_2$ to 20% MeOH/$CH_2Cl_2$) to give N-(2-(N-glycylaminomethyl)-5-tert-butyl-3-thienyl)-N'-(4-methylphenyl)urea (0.019 g, 48%): mp 93–6° C.; $^1$H NMR ($CDCl_3$) δ1.14 (s, 9H), 2.08 (s, 3H), 3.89 (s, 2H), 4.34 (br s, 7H), 6.67 (s, $^1$H), 6.87 (d, J=8.1 Hz, 2H), 7.12 (d, J=8.5 Hz, 2H), 7.3 (m, 2H).

Selected Compound Synthesized Using Method I
N-(2-(N-Acetylaminomethyl)-5-tert-butyl-3-thienyl)-N'-(4-methylphenyl)urea (Example 50): mp 203–5° C.; $^1$H NMR ($CDCl_3$/$d^6$-DMSO) δ1.3 (s, 9H), 1.9 (s, 3H), 2.2 (s, 3H), 4.3 (d, 2H), 7.0 (d, 2H), 7.2 (s, 1H), 7.3 (m, 2H), 8.6 (br s, 1H); FAB-LRMS m/z 360 (M+H).

Method J
Synthesis of N-(2-carbomethoxy-5-tert-butyl-3-thienyl)-N'-(4-methyl-2-thienyl)urea (Example 15).

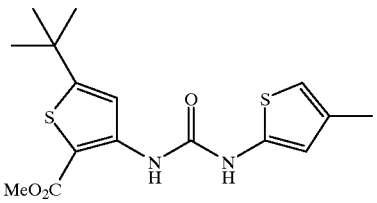

Step 1
A solution of 3-methylthiophene (5 mL, 51.75 mmol), sodium persulfate (18.48 g, 77.6 mmol) and palladium acetate (5.81 g, 25.88 mmol) in acetic acid (500 mL) was heated to the reflux temp. A slow stream of carbon monoxide was bubbled through the solution for 3 h. The reaction was cooled to 20° C. and concentrated under reduced pressure. The residue was dissolved in $CH_2Cl_2$. Celite® was added and the solution was filtered, then passed through a pad of silica gel, and concentrated under reduced pressure. The residue was dissolved in EtOAc and extracted with a 2N KOH solution. The aqueous layer was washed with EtOAc, the pH was adjusted to zero with a concentrated HCl solution, and the resulting mixture was extracted with EtOAc. The organic layer was washed with a saturated NaCl solution and concentrated under reduced pressure to yield a mixture of 3-methylthiophene-2-carboxylic acid and 4-methylthiophene-2-carboxylic acid (1.86 g, 25%).

Step 2
To a solution of a mixture of 3-methylthiophene-2-carboxylic acid and 4-methylthiophene-2-carboxylic acid (1.11 g, 7.81 mmol) and triethylamine (1.3 mL, 9.38 mmol) in acetone (75 mL) at −15° C. was slowly added ethyl chloroformate (1.12 mL, 11.72 mmol). The acetone solution was stirred for 15 min and a solution of NaN₃ (0.86 g, 13.3 mmol) in water (15 mL) was added. The reaction was stirred for 30 min, then diluted with CH₂Cl₂ and washed with a 1:1 v/v mixture of a saturated NaCl solution and water. The organic phase was dried (MgSO₄) and concentrated under reduced pressure. The residue was purified by flash chromatography (EtOAc/hexane) to give a mixture of azidoesters (0.91 g, 70%) which were used in the next step without further purification.

Step 3

The azidoester mixture (0.120 g, 0.72 mmol) was dissolved in toluene (3 mL) and heated to 100° C. for 5 h, then cooled to 20° C. Methyl 3-amino-5-tert-butylthiophene-2-carboxylate (0.11 g, 0.50 mmol) was added and the reaction was heated to 95° C. for 18 h. The reaction was cooled to 20° C. and concentrated under reduced pressure. The residue was purified by flash chromatography (EtOAc/hexane) followed by normal phase HPLC (CH₂Cl₂), to afford N-(2carbomethoxy-5-tert-butyl-3-thienyl)-N'-(4-methyl-2-thienyl)urea (0.082 g, 46%) and N-(2-carbomethoxy-5-tert-butyl-3-thienyl)-N'-(3-methyl-2-thienyl)urea (0.018 g, 10%). N-(2-Carbomethoxy-5-tert-butyl-3-thienyl)-N'-(3-methyl-2-thienyl)urea: $^1$H NMR (CDCl₃) δ1.35 (s, 9H), 2.15 (s, 3H), 3.75 (s, 3H), 6.45 (bs, 2H), 6.85 (d, 1H), 7.10 (d, 1H), 7.85 (s, 1H), 9.70 (s, 1H), FAB-LRMS m/z (rel abundance) 353 (M+H, 88%). N-(2-Carbomethoxy-5-tert-butyl-3-thienyl)-N'-(4-methyl-2-thienyl)urea: $^1$H NMR (CDCl₃) δ1.35 (s, 9H), 2.20 (s, 3H), 3.75 (s, 3H), 6.55 (bs, 2H), 7.80 (br s, 1H), 7.85 (s, 1H), 9.80 (s, 1H); FAB-LRMS m/z (rel abundance) 353 (M+H, 30%).

Selected Compound Synthesized Using Method J

N-(2-Carbomethoxy-5-tert-butyl-3-thienyl)-N'-(5-methyl-2-thienyl)urea (Example 14): mp 118–20° C.; $^1$H NMR (CDCl₃) δ1.35 (s, 9H), 2.40 (s, 3H), 3.75 (s, 3H), 6.55 (bs, 2H), 7.90 (s, 1H), 8.10 (bs, 1H), 9.75 (s, 1H); FAB-LRMS m/z (rel abundance) 353 (M+H, 56%).

Method K

Synthesis of N-(2-carbomethoxy-5-tert-butyl-3-furyl)-N'-(4-methylphenyl)urea (Example 32).

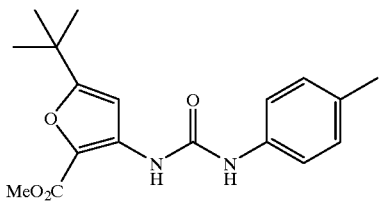

Step 1

To a solution of 2-tert-butylfuran (4.5 g, 36 mmol) in anh. THF (60 mL) at −78° C. under N₂ was added n-butyllithium (1.6M in hexane, 25 mL, 40 mmol, 1.1 equiv) dropwise. After 30 min, the cooling bath was replaced with an ice bath and the mixture was stirred at 0° C. for 1 h. Dry CO₂, generated from dry ice and dried over an anhydrous Na₂SO₄ tower, was bubbled into the reaction mixture over 20 min at −78° C. and then at 0° C. The reaction mixture was acidified to pH 1 with a 1M HCl solution, then extracted with EtOAc. The organic layer was washed with a concentrated NaCl solution, dried (NaSO₄) and concentrated under reduced pressure to give 5-tert-butylfuran-2-carboxylic acid as a pale yellow solid (4.2 g, 69%): $^1$H NMR (CDCl₃) δ1.29 (s, 9H), 6.11 (d 1H, J=3.3 Hz), 7.19 (d, 1H, J=3.3 Hz), 11.0 (br s, 1H).

Step 2

A solution of 5-tert-butylfuran-2-carboxylic acid (2.0 g, 11.9 mmol) in anh. THF (30 mL) was cooled to −78° C. under N₂, then n-butyllithium (1.6M in hexane solution, 15.6 mL, 25 mmol, 2.1 equiv) was added dropwise. After 30 min, TsN₃ (2.3 g, 11.9 mmol, 1.1 equiv) in anh. THF (3 mL) was added dropwise via cannula followed by a wash portion of anh. THF (3 mL). The yellow solution was allowed to warm to 0° C. over 2 h, then 6 g of KOAc (6 g, 60 mmol, 5 equiv) was added and the suspension was stirred rapidly at room temp. for 14 h. The mixture was diluted with Et₂O and extracted with water. The aqueous phase was acidified to pH 1 with a 1M HCl solution, then extracted thoroughly with EtOAc. The organic phase was washed with a concentrated NaCl solution, dried (NaSO₄), and concentrated under reduced pressure. The resulting red oil was diluted with Et₂O (150 mL) and MeOH (20 mL) then treated with TMSCHN₂ (2.0M in hexane, 45 mL, 90 mmol). After 30 min, the mixture was concentrated, and the oil was purified by flash chromatography (10% EtOAc/hexane) to give a colorless oil (1.72 g). Analysis of the product by $^1$H NMR indicated an approximately 2:3 mixture of methyl 3-azido-5-tert-butylfuran-2-carboxylate and methyl 5-tert-butylfuran-2-carboxylate, which co-elute. Methyl 3-azido-5-tert-butylfuran-2-carboxylate: $^1$H NMR (CDCl₃) δ1.25 (s, 9H), 3.80 (s, 3H), 5.99 (s, 1H); FTIR (neat) 2965 (s), 2118 (s), 1723 (s) cm⁻¹. The mixture was used in the next step without further purification.

Step 3

A mixture of methyl 3-azido-5-tert-butylfuran-2-carboxylate and methyl 5-tert-butylfuran-2-carboxylate (1.72 g) and 10% Pd/C (0.50 g) in cellosolve (30 mL) was successively evacuated and purged with H₂ three times. The reaction mixture was then shaken under H₂ (40 psi) for 1 h, diluted with EtOAc and filtered through a pad of Celite®. The filtrate was concentrated under reduced pressure, then purified by flash chromatography (20% EtOAc/hexane) to give methyl 5-tert-butylfuran-2-carboxylate (0.73 g, 34%) followed by methyl 3-amino-5-tert-butylfuran-2-carboxylate (0.59 g, 25% yield from 5-tert-butylfuran-2-carboxylic acid). Methyl 3-amino-5-tert-butylfuran-2-carboxylate: $^1$H NMR (CDCl₃) δ1.29 (s, 9H), 4.24 (br s, 2H), 5.76 (s, 1H); $^{13}$C NMR (CDCl₃) δ28.3, 32.8, 50.5, 98.3, 124.1, 144.9 (br), 160.5, 168.1, 178.7; FTIR (neat) 3330–2950 (br, s), 2850 (m), 1680 (s), 1637 (s), 1537 (s), 1346 (s), 1131 (s) cm⁻¹.

Step 4

Phosgene (1.93M in toluene, 1.3 mL, 2.5 mmol, 10 equiv) was added rapidly to a solution of methyl 3-amino-5-tert-butylfuran-2-carboxylate (0.050 g, 0.25 mmol) and anh. pyridine (1.0 mL) in anh. toluene (5 mL) at room temp. After 30 min, the orange suspension was concentrated under reduced pressure, then successively charged with dry toluene (1 mL) and concentrated (2×). Finally, anh. toluene (3 mL) was added followed by p-toluidine (0.100 g, 0.93 mmol, 3.7 equiv). The orange mixture was stirred overnight, diluted with EtOAc, washed with a 1M HCl solution and a concentrated NaCl solution, then dried (Na₂SO₄) and concentrated under reduced pressure. The residue was purified by flash chromatography to give N-(2-carbomethoxy-5-tert-butyl-3-furyl)-N'-(4-methylphenyl)urea (0.080 g, 96%) as a pale yellow oil: $^1$H NMR (CDCl₃) δ1.28 (s, 9H), 2.30 (s, 3H), 3.77 (s, 3H), 7.02 (s, 1H), 7.11 (d, J=8.1 Hz, 2H), 7.27 (d, J=8.1 Hz, 2H), 7.87 (br s, 1H), 8.68 (br s, 1H); $^{13}$C NMR (CDCl₃) δ20.6, 28.3 (3C), 33.0, 51.0, 100.1, 121.4 (2C), 126.0, 129.5 (2C), 134.0, 134.8, 137.7, 152.5, 160.5, 168.2; FTIR (neat) 3400–3200 (br, m), 2966 (s), 1676 (s), 1622 (s), 1536 (s), 1306 (s), 1097 (m) cm⁻¹.

Method L-1
Synthesis of N-(2-carbomethoxy-5-tert-butyl-3-furyl)-N'-(4-methylphenyl)urea (Example 32).

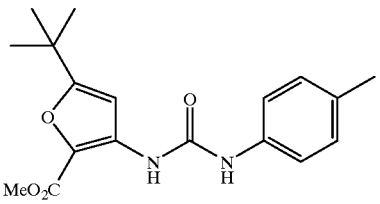

Step 1

3-Chloro-4,4dimethyl-2-pentenenitrile was prepared following a literature procedure (Hatcher et al. *J. Heterocycl. Chem.* 1989, 26, 1575). POCl$_3$ (22.4 mL), 0.24 mol, 2.4 equiv) was slowly added to a 0° C. solution of DMF (20.2 mL, 0.26 mol, 2.6 equiv) keeping the temp. under 20° C. The resulting pink solid was heated to 40° C., pinacolone (12.5 mL, 0.10 mol) was added to the resulting red solution, and this mixture was heated to 55° C. for 2 h and 75° C. for 2 h. NH$_2$OH.HCl (16.7 g, 0.24 mol, 2.4 equiv) was added to the 75° C. mixture slowly (<100 mg portions; CAUTION gas evolution and foaming). The resulting solution was heated to 85° C. for 2 h, then allowed to cool to room temp. overnight. The resulting yellow gel was separated between H$_2$O (500 mL) and EtOAc (300 mL). The aqueous layer was extracted with EtOAc (2×200 mL). The combined organic layers were washed with a saturated NaCl solution, dried (Na$_2$SO$_4$) and concentrated under reduced pressure to give 3-chloro-4,4-dimethyl-2-pentenenitrile as a brown oil (13.2 g, 93%): $^1$H NMR (CDCl$_3$) δ1.23 (s, 9H), 5.56 (s, 1H); GC-LRMS m/z (rel abundance) 143 (28%), 145 (11%). This material was used in the next step without further purification.

Step 2

To a slurry of NaH (5.98 g, 0.24 mol, 2.6 equiv) in anh. DME (800 mL) at 0° C. was added methyl glycolate (23.0 g, 0.26 mol, 2.8 equiv) over 20 min. The mixture was stirred for 1 h at room temp. and a solution of 3-chloro-4,4-dimethyl-2-pentenenitrile (13.1 g, 0.091 mol) in DME (100 mL) was added. The resulting solution was heated to 85° C. for 42 h, cooled to room temp., and treated with H$_2$O (100 mL). The resulting mixture was separated between H$_2$O (200 mL) and EtOAc (300 mL). The aqueous layer was extracted with EtOAc (2×200 mL). The combined organic layers were washed with a saturated NaCl solution, dried (Na$_2$SO$_4$), and concentrated under reduced pressure. The residual oil was purified by flash chromatography (300 g SiO$_2$, gradient from 50% CH$_2$Cl$_2$/hexane to 20% EtOAc/CH$_2$Cl$_2$) to give methyl 3-amino-5-tert-butylfuran-2-carboxylate as a yellow solid (2.98 g, 17%): mp 91–2° C.; TLC (20% EtOAc/hexane) R$_f$0.36; $^1$H NMR (CDCl$_3$) δ1.26 (s, 9H), 3.84 (s, 3H), 4.54 (br s, 2H), 5.75 (s, 1H); $^{13}$C NMR (CDCl$_3$) δ28.5 (3C), 33.0, 50.7, 98.5, 128.8, 131.0, 160.7, 168.3.

Step 3

To a solution of phosgene (1.93M in toluene, 9.7 mL, 18.6 mmol, 3.0 equiv) in CH$_2$Cl$_2$ (80 mL) at 0° C. was added a solution of methyl 3-amino-5-tert-butylfuran-2-carboxylate (1.23 g, 6.2 mmol) and pyridine (1.97 g, 24.9 mmol, 4.0 equiv) in CH$_2$Cl$_2$ (20 mL). The reaction mixture was allowed to slowly warm to room temp. and rapidly form a precipitate. The resulting slurry was stirred at room temp. for 1 h, then concentrated under reduced pressure to give 2-carbomethoxy-5-tert-butyl-3-furyl isocyanate and pyridinium hydrochloride. 2-Carbomethoxy-5-tert-butyl-3-furyl isocyanate: $^1$H NMR (CDCl$_3$) δ1.25 (s, 9H), 4.85 (s, 3H), 5.90 (s, 1H). The mixture was used in the next step without further purification.

Step 4

The 2-carbomethoxy-5-tert-butyl-3-furyl isocyanate prepared in Step 3 was dissolved in anh. toluene (40 mL), p-toluidine (2.05 g, 6.02 mmol, 1.0 equiv) was added, and the resulting solution was stirred at room temp. for 1 h. The toluene mixture was concentrated under reduced pressure, then diluted with CHCl$_3$ (150 mL). The organic solution was washed with a 1N HCl solution (2×100 mL) and a saturated NaCl solution (100 mL), dried (Na$_2$SO$_4$) and concentrated under reduced pressure. The residue was purified by flash chromatography (100 g SiO$_2$, gradient from hexane to 10% EtOAc/hexane) to give N-(2-carbomethoxy-5-tert-butyl-3-furyl)-N'-(4-methylphenyl)urea as a yellow solid (0.71 g, 35): mp 78–9° C.; TLC (20% EtOAc/hexane) R$_f$0.46; $^1$H NMR δ1.28 (s, 9H), 2.33 (s, 3H), 3.80 (s, 3H), 7.03 (s, 1H), 7.10 (br s, 1H), 7.15 (d, J=8.5 Hz, 2H), 7.27 (d, J=8.5 Hz, 2H) 8.60 (brs, 1H); $^{13}$C NMR δ20.8, 28.5 (3C), 33.2, 51.3, 100.3, 121.7 (br s, 2C), 126.2, 129.8 (br s, 2C), 134.3 (br s), 135.0, 137.5 (br s), 152.6, 160.8, 168.5; FAB-LRMS m/z (rel abundance) 331 (M+H, 64%).

Method L-2

Synthesis of ethyl 3-amino-5-tert-butylfuran-2-carboxylate.

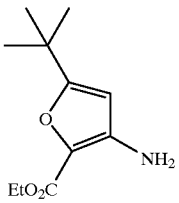

Step 1

A 0° C. solution of triphenylphosphine (2.72 g, 10.4 mmol, 1.3 equiv) in anh. THF (50 mL) was treated with diethyl azodicarboxylate (1.81 g, 10.4 mmol, 1.3 equiv), ethyl glycolate (1.08 g, 10.4 mmol, 1.3 equiv) and 4,4-dimethyl-3-oxopentanenitrile (1.00 g, 8.0 mmol). The resulting solution was allowed to warm to room temperature, stirred for 15 h and concentrated under reduced pressure. The residue was purified by flash chromatography (11 cm×22 cm SiO$_2$, gradient from 5% EtOAc/hex to 8% EtOAc/hex) to afford (Z)-4,4-dimethyl-3-(ethoxycarbonylmethoxy)pentenenitrile (1.36 g, 80%) as a colorless oil: TLC (5% EtOAc/hexanes) R$_f$0.26; $^1$H NMR (CDCl$_3$) δ1.12 (s, 9H), 1.28 (t, J=7.0 Hz, 3H), 4.24 (q, J=7.0 Hz, 2H), 4.55 (s, 1H), 5.00 (s, 2H); $^{13}$C NMR (CDCl$_3$) δ13.9, 27.8, 38.2, 61.5, 67.1, 67.3, 117.0, 167.1, 180.7; CI-LRMS m/z (rel abundance) 212 (M+H, 100%). Anal. Calcd for C$_{11}$H$_{17}$NO$_3$: C, 62.54; H, 8.11; N, 6.63. Found: C, 62.57; H, 7.90; N, 6.47.

Step 2

To a slurry of sodium hydride (62 mg, 2.6 mmol, 1.1 equiv) in anh. THF (50 mL) was added (Z)-4,4-dimethyl-3-(ethoxycarbonylmethoxy)pentenenitrile (0.50 g, 2.4 mmol). The reaction mixture was stirred for 3 h, treated with a saturated aq. NH$_4$Cl solution (2 mL), and concentrated under reduced pressure. The residue was purified by flash chromatography (50 g SiO$_2$, 10% EtOAc/hex) to afford ethyl 3-amino-5-tert-butylfuran-2-carboxylate (0.44 g, 88%) as a white solid: mp 44–45° C.; TLC (10% EtOAc/hex) R$_f$0.19; $^1$H NMR (CDCl$_3$) δ1.26 (s, 9H), 1.36 (t, J=7.0 Hz, 3H), 4.32

(q, J=7.0 Hz, 2H), 4.51 (br s, 2H), 5.75 (s, 1H); FAB-LRMS m/z (rel abundance) 212 (M+H, 100%). Anal. Calcd for $C_{11}H_{17}NO_3$: C, 62.54; H, 8.11; N, 6.63. Found: C, 62.48; H, 8.06; N, 6.61.

Selected Compound Synthesized Using Method L-1 or L-2

N-(2-Carbomethoxy-5-tert-butyl-3-furyl)-N'-4-fluorophenyl)urea (Example 33): mp 81–2° C.; TLC (20% EtOAc/hexane) $R_f$ 0.37; $^1$H NMR δ1.28 (s, 9H), 3.82 (s, 3H), 6.99 (s, 1H), 7.04 (app td, J=8.6, 2.2 Hz, 2H), 7.30–7.39 (m, 2H), 8.63 (brs, 1H); $^{13}$C NMR δ28.5 (3C), 33.3, 51.4, 100.2, 116.0 (d, $J_{C-F}$=22.0 Hz, 2C), 123.0 (br d, $J_{C-F}$=4.9 Hz, 2C), 126.3, 133.5 (d, $J_{C-F}$=3.7 Hz, 1C), 152.3, 159.8 (d, $J_{C-F}$=242.9 Hz, 1C), 168.6; FAB-LRMS m/z (rel abundance) 335 (M+H, 60%).

N-(2-Carbomethoxy-5-tert-butyl-3-furyl)-N'-(2,3-dichlorophenyl)urea (Example 34): mp 195–7° C.; TLC (20% EtOAc/hexane) $R_f$ 58; $^1$H NMR δ1.31 (s, 9H), 3.89 (s, 3H), 6.99 (s, 1H), 7.20–7.22 (m, 2H), 7.29 (s, 1H), 8.08 (dd, J=6.4, 3.5 Hz, 1H) 8.76 (brs, 1H); $^{13}$C NMR δ28.5 (3C), 33.3, 51.5, 100.1, 113.3, 119.7, 125.0, 126.5, 127.6, 132.9, 136.4, 137.5, 150.9, 161.1, 168.5; EI-LRMS m/z (rel abundance) 385 (M$^+$, 100%), 387 (M$^+$+2, 71%), 389 (M$^+$+4, 13%).

Method M

Synthesis of N-(2-methylcarbamoyl-5-tert-butyl-3-furyl)-N'-(4-fluorophenyl)urea (Example 36).

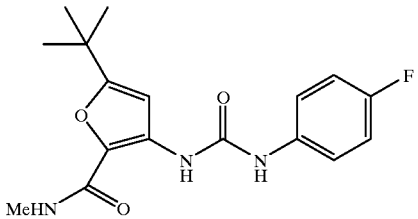

Step 1

A slurry of methylamine hydrochloride (1.03 g, 15.2 mmol, 3.0 equiv) in anh. toluene (60 mL) at 0° C. was treated with AlMe$_3$ (2M in toluene, 7.6 mL, 15.2 mmol, 3.0 equiv). The resulting solution was stirred at 0° C. for 30 min and allowed to warm to room temp for 40 min. To the aluminum amide solution was then added methyl 3-amino-5-tert-butyl-2-furancarboxylate (1.00 g, 5.1 mmol). The resulting mixture was heated at the reflux temp. for 20 h, cooled to room temp., and a 6N HCl solution was added dropwise. The quenched mixture was made basic with a 1N NaOH solution (approximately 100 mL) and extracted with EtOAc (3×200 mL). The combined organic layers were washed with a saturated NaCl solution, dried (Na$_2$SO$_4$), and concentrated under reduced pressure to afford N-methyl-3-amino-5-tert-butyl-2-furancarboxamide as a yellow solid (0.90 g, 91%): TLC (20% EtOAc/CH$_2$Cl$_2$) $R_f$ 0.26; $^1$H NMR (CDCl$_3$) δ1.23 (s, 9H), 2.93 (d, J=4.8 Hz, 3H), 4.51 (br s, 1H), 5.73 (s, 1H).

Step 2

To a solution of N-methyl-3-amino-5-tert-butylfuran-2-carboxamide (0.15 g, 0.76 mmol) in anh. toluene (2 mL) at the reflux temp. was slowly added 4-fluorophenyl isocyanate (0.10 g, 0.76 mmol, 1.0 equiv). The resulting solution was allowed to stir at the reflux temp. for 14 h, cooled to room temp., and concentrated under reduced pressure. The residue was purified by flash chromatography (15 g SiO$_2$, gradient from 50% CH$_2$Cl$_2$/hexane to 100% CH$_2$Cl$_2$, then to 20% EtOAc/CH$_2$Cl$_2$) to afford N-(2-methylcarbamoyl-5-tert-butylfuryl)-N'-(4-fluorophenyl)urea (0.16 g, 61%): mp 109–11° C., TLC (30% EtOAc/CH$_2$Cl$_2$) $R_f$ 0.21; $^1$H NMR (CDCl$_3$) δ1.29 (s, 9H), 2.89 (d, J=4.8 Hz, 3H), 6.02 (br q, J=4.8 Hz, 1H), 6.98 (app td, J=16.6, 4.1 Hz, 2H), 7.01 (s, 1H), 7.34–7.39 (m, 2H), 8.05 (br s, 1H), 9.14 (s, 1H); $^{13}$C NMR (CDCl$_3$) δ25.5, 28.7 (3C), 33.1, 100.7, 115.6 (d, $J_{C-F}$=23.2 Hz, 2C), 121.5 (d, $J_{C-F}$=7.3 Hz, 2C), 128.3, 134.5 (br s), 152.4, 158.9 (d, $J_{C-F}$=242.9 Hz, 1C), 161.6, 165.8; FAB-LRMS m/z (rel abundance) 334 (M+H, 100%).

Selected Compound Synthesized Using Method M

N-(2-Methylcarbamoyl-5-tert-butylfuryl)-N'-(4-methylphenyl)urea (Example 35): mp 190–3° C.; TLC (30% EtOAc/CH$_2$Cl$_2$) $R_f$ 0.25; $^1$H NMR (CDCl$_3$) δ1.29 (s, 9H), 2.30 (s, 3H), 2.92 (d, J=4.8 Hz, 3H), 5.99 (br q, J=4.8 Hz, 1H), 7.03 (d, J=1.1 Hz, 1H), 7.10 (d, J=8.5 Hz, 2H), 7.29 (d, J=8.5 Hz, 2H), 7.56 (br s, 1H), 9.12 (s, 1H); $^{13}$C NMR (CDCl$_3$) δ20.8, 25.4, 28.7 (3C), 33.8, 100.7, 120.1 (2C), 128.4, 129.7 (2C), 133.1, 134.5, 135.7, 152.3, 161.6, 165.6; FAB-LRMS m/z (rel abundance) 330 (M+H, 100%).

Method N-1

Synthesis of N-(2carbomethoxy-5-tert-butyl-3-pyrrolyl)-N'-(4-methyl-phenyl)urea (Example 38).

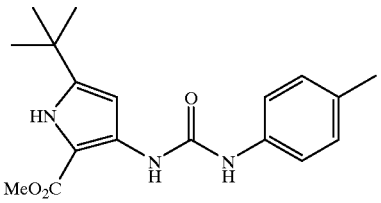

Step 1

To a solution of pyrrole-2-carboxylic acid (6.28 g, 56.5 mmol) in anh. MeOH (100 mL) under N$_2$ at room temp. was added TMSCl (17.9 mL, 141 mmol, 2.5 equiv) in one portion. After stirring overnight, the reaction mixture was concentrated under reduced pressure, redissolved in CH$_2$Cl$_2$, washed with water, dried (Na$_2$SO$_4$) and concentrated to give methyl pyrrole-2-carboxylate as a tannish semi-crystalline solid (4.62 g, 65%): $^1$H NMR (CDCl$_3$) δ3.86 (s, 3H), 6.29 (br q, 1H), 6.92 (br m, 1H), 6.96 (br m, 1H), 9.30 (br s, 1H). This material was used in the next step without further purification.

Step 2

To a solution of methyl pyrrole-2-carboxylate (0.30 g, 2.42 mmol) in anh. 1,2-dichloroethane (12 mL) under N$_2$ at room temp. was added AlCl$_3$ (0.710 g, 5.33 mmol, 2.2 equiv) in one portion. 2-Chloro-2-methylpropane (0.26 mL, 2.42 mmol, 1.0 equiv) was added in one portion via syringe. After 2 h, the reaction was quenched by slowly pouring it into a saturated NaHCO$_3$ solution. The resulting white suspension was extracted with Et$_2$O (2×). The combined organic layers were dried (Na$_2$SO$_4$) and concentrated under reduced pressure to give an off-white solid (0.40 g), which was purified by flash chromatography (60% CH$_2$Cl$_2$/hexane) to give methyl 5-tert-butylpyrrole-2-carboxylate as a white amorphous solid (0.36 g, 81%): $^1$H NMR (CDCl$_3$) δ1.31 (s, 9H), 3.83 (s, 3H), 6.00 (t, J=3.3 Hz, 1H), 6.81 (t, J=3.3 Hz, 1H), 8.82 (br s, 1H).

Step 3

To a heterogeneous mixture of methyl 5-tert-butylpyrrole-2-carboxylate (1.65 g, 9.10 mmol) in concentrated H$_2$SO$_4$ (19 mL) under N$_2$ at room temp. was added fuming nitric acid (0.57 mL, 13.6 mmol, 1.5 equiv) in one portion via syringe. After 1 h, the reaction mixture was poured into ice-water and the resulting mixture was carefully adjusted to pH 7 with solid Na$_2$CO$_3$. The resulting mixture was extracted with Et₂O (2×), dried (Na₂SO₄), and concentrated under reduced pressure. The residue was purified using flash chromatography (70% CH₂Cl₂/hexane) to give methyl 5-tert-butyl-3,4-dinitropyrrole-2-carboxylate (0.27 g) followed by methyl 5-tert-butyl-3-nitropyrrole-2-carboxylate (0.44 g). Resubmission of mixed fractions to the flash chromatography conditions provided additional methyl 5-tert-butyl-3-nitropyrrole-2-carboxylate (0.22 g, 0.66 g total, 32% total yield). Methyl 5-tert-butyl-3-nitropyrrole-2-carboxylate: $^1$H NMR (CDCl₃) δ1.33 (s, 9H), 3.93 (s, 3H), 6.56 (d, J=3.3 Hz, 1H), 9.22 (br s, 1H). Methyl 5-tert-butyl-3,4-dinitropyrrole-2-carboxylate: $^1$H NMR (CDCl₃) δ1.52 (s, 9H), 3.91 (s, 3H), 9.17 (br s, 1H).

Step 4

A mixture of methyl 5-tert-butyl-3-nitropyrrole-2-carboxylate (0.014 g, 0.062 mmol) and 10% Pd/C (3 mg) in dry MeOH (1 mL) was successively evacuated and purged with H₂ three times, then shaken under an atmosphere of H₂ (35 psi) for 1 h, diluted with CH₂Cl₂ and filtered through a pad of Celite®. The filtrate was concentrated under reduced pressure to give methyl 3-amino-5-tert-butylpyrrole-2-carboxylate as a bright yellow oil (0.012 g, 100%). $^1$H NMR (CDCl₃) δ1.26 (s, 9H), 3.82 (s, 3H), 5.52 (d, J=2.8 Hz, 1H), 7.89 (br s, 2H). This material was used in the next step without further purification.

Step 5

To a solution of methyl 3-amino-5-tert-butylpyrrole-2-carboxylate (12 mg, 0.062 mmol) and anh. pyridine (0.25 mL, 3.06 mmol, 49.4 equiv) in anh. toluene (1 mL) was rapidly added phosgene (1.93M in toluene, 0.32 mL, 0.62 mmol, 10 equiv). After 30 min, the orange suspension was concentrated under reduced pressure, then successively charged with anh. toluene (1 mL) and concentrated (2×). Finally, toluene (2 mL) was added followed by p-toluidine (10 mg, 0.094 mmol). The mixture was heated at 90° C. for 3 h, then was concentrated under reduced pressure. The residue was purified by preparative TLC (2 plates, 20×20 cm×0.25 mm, 2% MeOH/CH₂Cl₂). The major UV-active band was isolated and the product was extracted from the silica using 5% MeOH/CH₂Cl₂ to give N-(2-carbomethoxy-5-tert-butyl-3-pyrrolyl)-N'-(4-methylphenyl)urea as a pale yellow amorphous solid (0.016 g, 80%): $^1$H NMR (d⁶-DMSO) δ1.23 (s, 9H), 2.20 (s, 3H), 3.78 (s, 3H), 6.54 (d, J=3.0 Hz, 1H), 7.04 (d, J=8.5 Hz, 2H), 7.32 (d, J=8.5 Hz, 2H), 8.61 (s, 1H), 9.51 (s, 1H), 10.85 (br d, J=2.2 Hz, 1H); $^{13}$C NMR (MeOD, CDCl₃, partial spectrum) δ19.7, 29.0 (3C), 31.5, 50.0, 97.4, 105.9, 119.6 (2C), 128.9 (2C), 132.2, 136.2, 147.6, 153.5, 161.9; FTIR (KBr) 3341 (s), 2947 (m), 1676 (s), 1583 (s), 1548 (s), 1456 (s), 1279 (s), 1208 (s), 1094 (s); cm⁻¹; FAB-LRMS m/z (rel abundance) 330 (M+H, 47%).

Selected Compounds Synthesized Using Method N-1:

N-(2-Carbomethoxy-5-tert-butyl-3-pyrrolyl)-N'-(phenyl)urea (Example 37): $^1$H NMR (d⁶-DMSO) δ1.23 (s, 9H), 3.78 (s, 3H), 6.54 (d, J=2.9 Hz, 1H), 7.26 (dd, J=2.6, 8.8 Hz, 1H), 7.48 (d, J=8.8 Hz, 1H), 7.90 (d, J=2.6 Hz, 1H), 8.76 (s, 1H), 9.97 (s, 1H), 9.97 (s, 1H), 10.95 (br d, J=1.8 Hz, 1H); FAB-LRMS m/z (rel abundance) 384 (M+H, 93%).

N-(2-Carbomethoxy-5-tert-butyl-3-pyrrolyl)-N'-(2,3-dichlorophenyl)urea (Example 39): $^1$H NMR (d⁶-DMSO) δ1.23 (s, 9H), 3.78 (s, 3H), 6.55 (d, J=2.9 Hz, 1H), 6.92 (t, J=7.4 Hz, 1H), 7.23 (dd, J=7.4, 8.5 Hz, 2H), 7.44 (d, J=7.7 Hz, 2H), 8.66 (s, 1H), 9.60 (s, 1H), 10.88 (br d, J=1.5 Hz, 1H); FAB-LRMS m/z (rel abundance) 316 (M+H, 95%).

Method N-2

Synthesis of N-(2-carbomethoxy-5-tert-butyl-3-pyrrolyl)-N'-(2,3-dichlorophenyl)urea (Example 73).

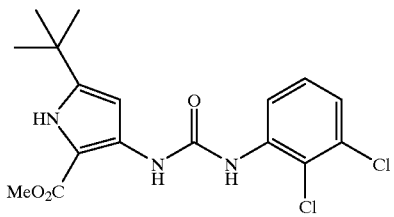

To a solution of methyl 3-amino-5-tert-butylpyrrole-2-carboxylate (0.99 g, 5.00 mmol) in anh. CH₂Cl₂ (50 ml) at room temp. was added a solution of 2,3-dichlorophenyl isocyanate (0.948 g, 5.00 mmol) in CH₂Cl₂ (10 mL) and the resulting mixture was allowed to stir overnight. The resulting white precipitate formed overnight was separated and washed with CH₂Cl₂ to give the desired urea (1.39 g, 67%) as a white powder: mp 200–201° C.; $^1$H-NMR (DMSO-d₆) δ1.23 (s, 9H), 3.78 (s, 3H), 6.50 (d, J=2.95 Hz, 1H), 7.26–7.30 (m, 2H), 7.88–7.91 (m, 1H), 9.12 (s, 1H), 9.40 (s, 1H), 10.91 (br s, 1H); FAB-LRMS m/z 384 (M+H). Anal. Calcd for C₁₇H₁₉N₃O₃Cl₂: C, 53.14; H, 4.98; N, 10.94. Found: C, 53.03; H, 4.79; N, 10.86.

Method N-3

Synthesis of N-(2-methylcarbamoyl-5-tert-butyl-3-pyrrolyl)-N'-(4-methylphenyl)urea (Example 113).

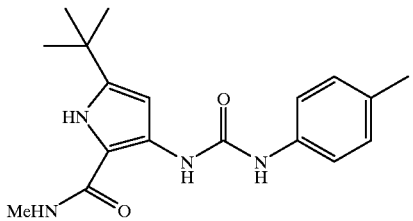

Step 1

Methyl 5-tert-butyl-3-nitropyrrole-2-carboxylate was prepared as described in Method N-1 Step 3. To a solution of methyl 5-tert-butyl-3-nitropyrrole-2-carboxylate (10.38 g, 45.9 mmol) in a THF—MeO—H₂O mixture(1.0:1.0:0.5, 250 mL) at room temp. was added a 1N NaOH solution (92 mL, 92 mmol) via pippette. The color of the reaction mixture turned from green to red. The mixture was warmed to the reflux temperature, maintained for 3 hr, cooled to room temp. and concentrated in vacuo. The residue was made acidic using a 10% citric acid solution and was extracted with EtOAc (2×50 mL). The organic layer was washed with a saturated NaCl solution, dried (MgSO₄), and concentrated in vacuo. The residue was triturated with hexanes to give 5-tert-butyl-3-nitropyrrole-2-carboxylic acid (9.70 g, 99%) as a green powder: $^1$H NMR (DMSO-d₆) δ1.24 (s, 9H), 6.41 (d, J=2.9 Hz, 1H), 12.19 (br s, 1H), 13.50 (br s, 1H).

Step 2

To a solution of 5-tert-butyl-3-nitropyrrole-2-carboxylic acid (2.01 g, 9.5 mmol) in a solution of anh. THF and anh. DMF (3:1, 100 mL) at 0° C. was added N-methylmorpholine (2.1 mL, 19 mmol, 2.0 equiv), followed by methylamine (2M in THF, 5.93 mL, 11.1 mmol, 1.25 equiv) and EDCI·HCl (2.85 g, 14.9 mmol, 1.57 equiv). The resulting mixture was allowed to warm to room temp. and stirred at that temp. overnight. The reaction mixture was diluted with H₂O (100 mL), then made acidic with a 10% citric acid solution, and extracted with EtOAc (2×50 mL). The combined organic layers were washed with a saturated NaCl solution, dried (MgSO$_4$), and concentrated in vacuo. The residue was purified by flash chromatography (15% CH$_2$Cl$_2$/hex) to give 2-(N-methylcarbamoyl)- 5-tert-butyl-3-nitropyrrole (1.40 g, 66%) as a yellow solid: $^1$H NMR (DMSO-d$_6$) δ1.29 (s, 9H), 2.76 (d, J=4.4 Hz, 3H), 6.36 (d, 2.9 Hz, 1H), 8.59–8.60 (m, 1H), 12.19 (br s, 1H).

Step 3

To a solution of 2-(N-methylcarbamoyl)-5-tert-butyl-3-nitropyrrole (1.0 g, 0.4 mmol) in EtOAc (50 mL) under an Ar atmosphere was added 10% Pd/C (50 mg). The mixture was evacuated then placed under a static H$_2$ atmosphere (1 atm.) for 24 h. The resulting slurry was filtered through a pad of Celite® with the aid of EtOAc, and the filtrate was concentrated under reduced pressure to afford 2-(N-methylcarbamoyl)-3-amino-5-tert-butylpyrrole (0.61 g, 70%): $^1$H-NMR (DMSO-d$_6$) δ1.16 (s, 9H), 2.66 (d, J=4.41 Hz, 3H), 4.89 (br s, 2H), 5.27 (d, 2.58 Hz, 1H), 7.14–7.16 (m, 1H), 9.52 (br s, 1H).

Step 4

To a solution of 2-(N-methylcarbamoyl)-3-amino-5-tert-butylpyrrole (0.14 g, 0.70 mmol) in CH$_2$Cl$_2$ (5 mL) at room temp. was annd p-tolyl isocyanate (0.088 mL, 0.70 mmol, 1.0 equiv) and the resulting mixture was allowed to stir at room temp. overnight. The resulting precipitate was separated and washed with CH$_2$Cl$_2$ to give N-(2-methylcarbamoyl-5-tert-butyl-3-pyrrolyl)-N'-(4-methylphenyl)urea (0.17 g, 74%): mp 164–166° C.; $^1$H-NMR (DMSO-d$_6$) δ1.23 (s, 9H), 2.19 (s, 3H), 2.75 (d, J=4.41 Hz, 3H), 6.49 (d, J=2.57 Hz, 1H), 7.01 (d, J=8.46 Hz, 2H), 7.33 (d, J=8.46 Hz, 2H), 7.60–7.63 (m, 1H), 9.45 (s, 1H), 9.50 (s, 1H), 10.17 (br s, 1H); FAB-LRMS m/z 329 (M+H).

Method O

Synthesis of N-(N-methyl-2-carbomethoxy-5-tert-butyl-3-pyrrolyl)-N'-(4-methylphenyl)urea (Example 40).

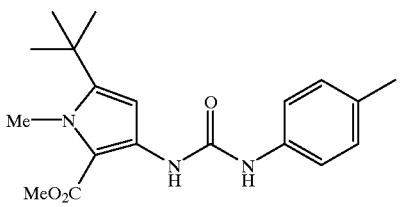

Step 1

To a cold (0–10° C.) solution of methyl 5-tert-butyl-3-nitropyrrole-2-carboxylate (0.100 g, 0.44 mmol), benzyltributylammonium bromide (0.16 mg, 0.44 mmol, 1 equiv), and dimethyl sulfate (46 μL, 0.49 mmol, 1.1 equiv) in CH$_2$Cl$_2$ (1 mL) was added a 50% NaOH solution (0.21 g, 2.65 mmol, 6 equiv). After 5 min, the cooling bath was removed and the mixture was stirred at room temp. for 4 h. The reaction mixture was diluted with CH$_2$Cl$_2$, washed with water and a 10% NH$_4$OAc solution (2x), dried (Na$_2$SO$_4$), and concentrated under reduced pressure to give a bright yellow oil. The oil was purified by flash chromatography (70% CH$_2$Cl$_2$/hexane) to give methyl 5-tert-butyl-1-methyl-3-nitropyrole-2-carboxylate as a pale yellow oil which solidifies upon standing (0.061 g, 62%): $^1$H NMR (CDCl$_3$) δ1.38 (s, 9H)., 3.80 (s, 3H), 3.92 (s, 3H), 6.47 (s, 1H).

Step 2

Methyl 5-tert-butyl-1-methyl-3-nitropyrrole-2-carboxylate was reduced in a manner similar to that described in Method N, Step 4 to give methyl 3-amino-5-tert-butyl-1-methylpyrrole-2carboxylate as an oil (0.059 g, 100%, crude yield): $^1$H NMR (CDCl$_3$) δ1.33 (s, 9H), 3.80 (s, 3H), 3.85 (s, 3H), 4.34 (br s, 2H), 5.48 (s, 1H); $^{13}$C NMR (CDCl$_3$) δ29.7, 31.9, 34.7, 50.6, 95.7, 107.4, 142.3, 149.0, 162.2.

Step 3

To a solution of methyl 3-amino-5-tert-butyl-1-methylpyrrole-2-carboxylate (0.059 g, 0.280 mmol) and dry pyridine (1 mL) in anh. toluene (2 mL) was rapidly added phosgene (1.93M in toluene, 1.45 mL, 2.80 mmol, 10 equiv). Additional anh. toluene (3 mL) was added to aid stirring of the heterogeneous mixture. After 30 min, the orange suspension was concentrated under reduced pressure, then successively charged with anh. toluene (1 mL) and evaporated (2x). Finally, toluene (3 mL) was added followed by p-toluidine (0.11 mg, 1.04 mmol, 3.7 equiv). The resulting homogeneous mixture was stirred overnight, diluted with CH$_2$Cl$_2$ and washed with a $^1$M HCl solution. The aqueous layer was back-extracted with CH$_2$Cl$_2$ (2x). The combined organic phases were dried (Na$_2$SO$_4$), and concentrated under reduced pressure. The residue was purified by flash chromatography (10% to 25% EtOAc/hexane) to give N-(N-methyl-2-carbomethoxy-5-tert-butyl-3-pyrrolyl)-N'-(4methyl-2-thienyl)urea as a pale yellow solid (0.066 g, 69%): $^1$H NMR (CDCl$_3$) δ1.35 (s, 9H), 2.31 (s, 3H), 3.64 (s, 3H), 3.88 (s, 3H), 6.80 (s, 1H), 7.11 (d, J=8.4 Hz, 2H), 7.26 (app d, J=8.4 Hz, 3H), 8.81 (br s, 1H); $^{13}$C NMR (CDCl$_3$) δ29.8 (3C), 31.4, 32.1, 35.0, 50.4, 98.8, 108.8, 122.0 (2C), 129.5 (2C), 133.8, 134.0, 135.3, 148.6, 153.0, 162.0; FTIR (KBr) 2364 (s), 2335 (s), 1659 (m), 1579 (m), 1542 (m), 1354 (w), 1232 (w) cm$^{-1}$.

Method P

Synthesis of N-(3-carbomethoxy-5-tert-butyl-2-thienyl)-N'-(4-methylphenyl)urea (Example 44).

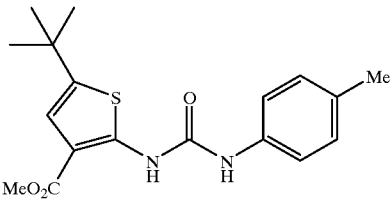

Step 1

To a solution of methyl cyanoacetate (4.00 g, 40.4 mmol), sulfur (1.29 g, 40.4 mmol) and DMF (20 mL) at room temp. was added Et$_3$N (3.04 mL, 21.8 mmol). 3,3-Dimethylbutraldehyde (5.08 g, 40.4 mmol) was added and the mixture was stirred 1 h before being poured into water (200 mL). Solids were removed by filtration and the filtrate was extracted with EtOAc. The organic layer was filtered through a plug of silica gel and concentrated under reduced pressure. The crude product was purified via flash chromatography to afford methyl 2-amino-5-tert-butylthiophene-3-carboxylate (4.19 g, 49%).

Step 2

Methyl 2-amino-5-tert-butylthiophene-3-carboxylate was condensed with 4-methylphenyl isocyanate in a manner similar to that described in Method A, Step 2 to produce N-(2-carbomethoxy-5-tert-butyl-3-thienyl)-N'-(4-methylphenyl)urea (0.029 g, 18%): mp 109–111° C.; $^1$H NMR (CDCl$_3$) δ1.38 (s, 9H), 2.34 (s, 3H), 3.81 (s, 3H), 6.75 (bs, 1H), 6.82 (s, 1H), 7.16 (d, J=8.1 Hz, 2H), 7.32 (d, J=8.5 Hz, 2H), 10.37 (s, 1H).

Selected Compound Synthesized Using Method P

N-(3-Carbomethoxy-5-tert-butyl-2-thienyl)-N'-(phenyl)urea (Example 43): mp 80–2° C.; $^1$H NMR (CDCl$_3$) δ1.36

(s, 9H), 3.83 (s, 3H), 6.73 (br s, 1H), 6.84 (s, 1H), 7.16 (t, J=7.4 Hz, 1H), 7.37 (app t, J=7.4 Hz, 2H), 7.52 (dd, J=8.1, 1.5 Hz 2H), 10.43 (br s, 1H); $^{13}$C NMR (CDCl$_3$) δ32.2 (3C), 34.2, 51.7, 109.9, 117.0, 121.3 (2C), 124.8, 129.4 (2C), 137.7, 146.0, 149.6, 151.8, 166.4; EI-LRMS m/z 333 (M$^+$).

Method Q

Synthesis of N-(3-carbomethoxy-5-isopropyl-2-thienyl)-N'-(4-methylphenyl)urea (Example 42).

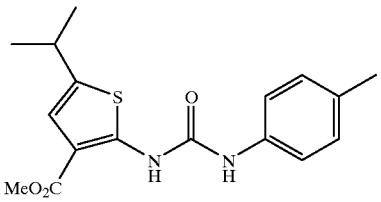

Methyl 2-amino-5-isopropylthiophene-3-carboxylate was synthesized in a manner analogous to that described in Method P, Step 1.

To a solution of methyl 2-amino-5-isopropyllthiophene-3-carboxylate (0.20 g, 1.00 mmol) in anh.CH$_2$Cl$_2$ (10 mL) was added phosgene (1.93M in toluene, 2.1 mL, 4.01 mmol, 4.0 equiv) and anh. pyridine (0.32 mL, 4.01 mmol, 4.0 equiv). The CHCl$_3$ mixture was allowed to warm to room temp. and was stirred for 3 h. The resulting mixture was concentrated under reduced pressure. The residue was suspended in anh. toluene (10 mL) and p-toluidine (0.11 mg, 1.00 mmol, 1.0 equiv) was added. The resulting mixture was stirred overnight then separated between EtOAc (50 mL) and H$_2$O (50 mL). The organic phase was washed with a 1M HCl solution (2×25 mL), a saturated NaHCO$_3$ solution (2×20 mL) and a saturated NaCl solution (2×25 mL), dried (MgSO$_4$) and concentrated under reduced pressure. The residue was purified by rotary chromatography (CH$_2$Cl$_2$), followed by preparative HPLC (SiO$_2$, 10% EtOAc/hexane) to give N-(3-carbomethoxy-5-isopropyl-2-thienyl)-N'-(4-methylphenyl)urea (0.15 g, 45%): mp 49–51° C.; $^1$H NMR (CDCl$_3$) δ1.29 (d, J=6.6 Hz, 6H), 2.34 (s, 3H), 3.02 (sept d, J=6.4, 1.1 Hz, 1H), 3.80 (s, 3H), 6.81 (s, 1H), 6.96 (br s, 1H), 7.17 (d, J=8.5 Hz, 2H), 7.32 (d, J=8.5 Hz, 2H), 10.4 (s, 1H); FAB-LRMS m/z 333 (M+H).

Selected Compound Synthesized Using Method Q

N-(3-Carbomethoxy-5-isopropyl-2-thienyl)-N'-(phenyl) urea (Example 41): mp 64–5° C.; $^1$H NMR (CDCl$_3$) δ1.29 (d, J=7.0 Hz, 6H), 3.02 (sept d, J=6.8, 1.1 Hz, 1H), 3.80 (s, 3 H), 6.82 (d, J=1.1 Hz, 1H), 7.07 (br s, 1H), 7.16 (t, J=7.4 Hz, 1H), 7.37 (app t, J=7.9 Hz, 2H), 7.46 (dd, J=8.8, 1.5 Hz, 2H), 10.4 (s, 1H); FAB-LRMS m/z 319 (M+H).

Method R

Synthesis of N-(2carboxy-5-tert-butyl-3-thienyl)-N'-(3,4-dichlorophenyl)urea (Example 66).

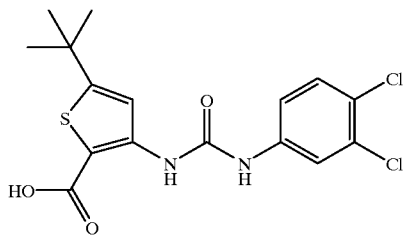

Step 1

A mixture of methyl 5-tert-butyl-3-aminothiophene-2-carboxylate (6.39 g, 30.0 mmol) and KOH (5.04 g, 90.0 mmol) in aqueous MeOH (1:1; 40 mL) was stirred at 80–90° C. for 6 h and the resulting clear solution was concentrated under reduced pressure. The gummy yellow residue was dissolved in H$_2$O (500 mL), treated with a phosgene solution (20% in toluene; 60 mL) dropwise over 2 h and stirred at room temp. overnight. The resulting yellow solids were removed by filtration, triturated with acetone (30 mL), and dried under reduced pressure to afford 7-tert-butyl-2H-thieno[3,2-d]oxazine-2,4(1H)-dione (4.25 g, 63%): $^1$H-NMR (CDCl$_3$) δ1.38 (s, 9H), 2.48 (s, 1H), 6.75 (s, 1H); FAB-MS m/z (rel abundance) 226 ((M+H)$^+$, 100%).

Step 2

To a solution of 7-tert-butyl-2H-thieno[3,2-d]oxazine-2,4(1H)-dione (0.18 g, 0.80 mmol) in THF (6 mL) was added 3,4-dichloroaniline (0.14 g, 0.86 mmol). The resulting mixture was stirred at 70° C. for 4 h, treated with Dowex 50WX2 resin (0.060 g) and poly(4-(4-hydroxymethylphenoxy)methylstyrene) resin (0.4 g) and stirred at 70° C. for an additional 30 min. The resulting slurry was filtered, and the filtrate was concentrated under reduced pressure to give N-(2-carboxy-5-tert-butyl-3-thienyl)-N'-(3,4-dichlorophenyl)urea (0.061 g, 20%): HPLC ES-MS m/z (rel abundance) 386 ((M+H)$^+$).

Method S

Synthesis of N-(3-carbomethoxy-5-tert-butyl-2-thienyl)-N'-(3-methylphenyl)urea (Example 122).

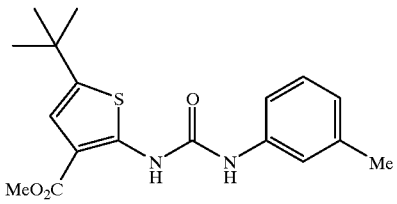

Step 1

To a solution of trichloromethyl chloroformate (diphosgene; 7.0 g, 35.3 mmol) in CH$_2$Cl$_2$ (100 mL) was added methyl 2-amino-5-tert-butylthiophene-3-carboxylate (5.0 g, 23.5 mmol) and pyridine (2.8 g, 35.3 mmol). The reaction mixture was heated to the reflux temp. for 10 h, filtered through a pad of silica, and concentrated under reduced pressure. The residue was dissolved in toluene and the resulting solution was concentrated under reduced pressure to give 3-methoxycarbonyl-5-tert-butylthiophene-2-isocyanate contaminated with a side product. 3-Methoxycarbonyl-5-tert-butylthiophene-2-isocyanate: $^1$H-NMR (CDCl$_3$) δ1.34 (s, 9H), 3.88 (s, 3H), 6.95 (s, 1H). Side product: $^1$H-NMR (CDCl$_3$) d 1.37 (s, 9H), 3.89 (s, 3H), 6.88 (s, 1H), 10.92 (br s, 1H). This material was used in the next step without further purification.

Step 2

A solution of 3-methoxycarbonyl-5-tert-butylthiophene-2-isocyanate in toluene (0.16M, 2.5 mL 0.4 mmol) was added to 3-methylaniline (0.053 g, 0.5 mmol). The resulting mixture was stirred at 60° C. for 4 h, cooled to room temp., then treated with a 2M H$_2$SO$_4$ solution (0.7 mL). EtOAc (4 mL) was added and the mixture was stirred vigorously. The mixture was passed through a filtration cartridge (0.8 g Extrelute® and 3 g silica gel) with the aid of EtOAc (8 mL), then concentrated under reduced pressure (speedvac: 2 h at 43° C.; 1 h at 60° C.) to afford N-(3-carbomethoxy-5-tert-butyl-2-thienyl)-N'-3-methylphenyl)urea (0.11 g, 80%): $^1$H-NMR (CDCl$_3$) δ1.35 (s, 9H), 2.36 (s, 3H), 3.82 (s, 3H), 6.82 (s, 1H), 6.93–7.01 (m, 2H), 7.13–7.29 (m, 2H), 7.35 (br s, 1H), 10.44 (s, 1H).

Method T
Synthesis of N-(3-carbomethoxy-5-tert-butyl-2-thienyl)-N'-(4-dimethylaminophenyl)urea (Example 142).

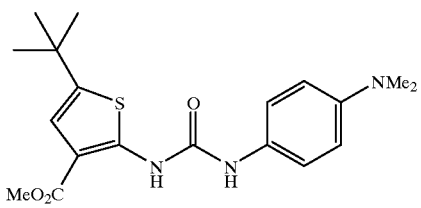

A solution of 3-methoxycarbonyl-5-tert-butylthiophene-2-isocyanate in toluene (0.16M, 2.5 mL 0.4 mmol) was added to 4-(N,N-dimethylamino)aniline (0.054 g, 0.4 mmol). The reaction mixture was stirred at 60° C. for 4 h, then concentrated under reduced pressure (speedvac: 2 h at 43° C.; 1 h at 60° C.). The crude product was purified by flash chromatography (SiO$_2$, EtOAc/pet. ether) to afford N-(3-carbomethoxy-5-tert-butyl-2-thienyl)-N'-(4-dimethylaminophenyl)urea (0.099 g, 66%): $^1$H-NMR (CDCl$_3$) δ1.35 (s, 9H), 3.0 (br s, 6H), 3.75 (s, 3H), 6.6–7.0 (m, 3H), 7.1–7.5 (m, 3H), 10.25 (br s, 1H).

Method U
Synthesis of N-(3carbamoyl-5-tert-butyl-2-thienyl)-N'-(4-methylphenyl)urea (Example 119).

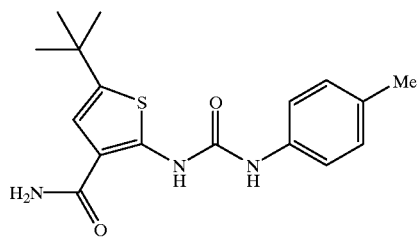

Step 1

A mixture of α-cyanoacetamide (1.68 g, 20 mmol), sulfur (0.64 g, 20 mmol) and 3,3-dimethylbutanal (2.0 g, 20 mmol) in MeOH (20 mL) was heated to the reflux temp. and morpholine (1.74 g, 20 mmol) was added within 10 min. The reaction mixture was stirred at the reflux temp. for 8.5 h, then concentrated under reduced pressure. The residue was purified by flash chromatography (50% EtOAc/50% pet. ether) to give 2-amino-5-tert-butylthiophene-3-carboxamide (2.94 g, 74%): $^1$H-NMR (CDCl$_3$) δ1.3 (s, 9H), 5.48 (br s, 4H), 6.37 (s, 1H).

Step 2

A solution of 2-amino-5-tert-butylthiophene-3-carboxamide (0.14 g, 0.7 mmol) and p-tolyl isocyanate (0.093 g, 0.7 mmol) in toluene (5 mL) was stirred at 60° C. overnight. The reaction mixture was separated between with water (10 mL) and EtOAc (10 mL). The aqueous phase was back-extracted with EtOAc (3×10 mL), and the combined organic phases were washed with a saturated NaCl solution (25 mL), dried (Na$_2$SO$_4$), and concentrated under reduced pressure. The residue was purified by chromatography (SiO$_2$; gradient from 20% EtOAc/80% pet. ether to 30% EtOAc/70% pet ether) to give N-(3-carbamoyl-5-tert-butyl-2-thienyl)-N'-(4-methylphenyl)urea (0.092 g, 40%): $^1$H-NMR (CDCl$_3$) δ1.38 (s, 9H), 2.32 (s, 3H), 5.58 (br s, 2H), 6.53 (s, 1H), 7.13 (app d, 2H), 7.35 (app d, 2H), 7.45 (br, 1H), 11.23 (br s, 1H).

The following compounds have been synthesized according to the general methods listed above:

TABLE 1

3-Urido Thiophenes

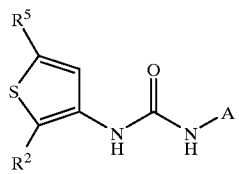

| # | R$^2$ | R$^5$ | A | mp (° C.) | TLC (R$_f$) | TLC Conditions | MS | MS Source | Method |
|---|---|---|---|---|---|---|---|---|---|
| 1 | CO$_2$Me | iPr | C$_6$H$_5$ | 108–10 | | | | | A |
| 2 | CO$_2$Me | tert-Bu | C$_6$H$_5$ | 106–8 | | | | | A |
| 3 | CO$_2$iPr | tert-Bu | C$_6$H$_5$ | 65–7 | | | | | D |
| 4 | CO$_2$H | tert-Bu | 4-MeC$_6$H$_4$ | | | | 333 (M + H) | FAB | H |
| 5 | CO$_2$Me | tert-Bu | 4-MeC$_6$H$_4$ | 124–6 | | | | | A |
| 6 | CO$_2$Et | tert-Bu | 4-MeC$_6$H$_4$ | | | | 360 (M$^+$) | EI | D |
| 53 | CO$_2$Pr-n | tert-Bu | 4-MeC$_6$H$_4$ | 59–66 | 0.38 | 10% EtOAc/ 90% hex | 375 (M + H) | FAB | E |
| 7 | CO$_2$iPr | tert-Bu | 4-MeC$_6$H$_4$ | 72–86 | 0.34 | 10% EtOAc/ 90% hex | 375 (M + H) | FAB | E |

TABLE 1-continued

3-Urido Thiophenes

| # | R² | R⁵ | A | mp (° C.) | TLC (R_f) | TLC Conditions | MS | MS Source | Method |
|---|---|---|---|---|---|---|---|---|---|
| 8 | CO₂All | tert-Bu | 4-MeC₆H₄ | 52–62 | 0.34 | 10% EtOAc/ 90% hex | 373 (M + H) | FAB | E |
| 9 | CO₂Me | tert-Bu | 3-MeC₆H₄ | 70–2 | | | 347 (M + H) | FAB | B |
| 54 | CO₂Me | tert-Bu | 4-FC₆H₄ | 160–2 | 0.45 | 20% EtOAc/ 80% hex | 351 (M + H) | FAB | B |
| 10 | CO₂Me | tert-Bu | 2-HOC₆H₄ | 75–7 | | | | | B |
| 11 | CO₂Me | tert-Bu | 2-H₂NC₆H₄ | | | | 348 (M + H) | FAB | C |
| 13 | CO₂Me | tert-Bu | 3,4-Me₂C₆H₃ | 68–71 | | | | | A |
| 14 | CO₂Me | tert-Bu | (2,5-dimethylthiophen-3-yl) | 118–20 | | | 353 (M + H) | FAB | J |
| 15 | CO₂Me | tert-Bu | (2-methyl-4-methylthiophen-5-yl) | | | | 353 (M + H) | FAB | J |
| 16 | CO₂Me | tert-Bu | (5-cyclopropyl-2-methyl-1,3,4-thiadiazol) | 188–9 | | | 381 (M + H) | FAB | B |
| 17 | CO₂Me | tert-Bu | (1-naphthyl-methyl) | 109–11 | | | | | A |
| 18 | CO₂Me | tert-Bu | (quinolin-5-yl-methyl) | 181–2 | | | | | B |
| 19 | CO₂Me | tert-Bu | (1H-indol-4-yl-methyl) | 92–3 | | | | | B |
| 55 | CO₂Me | tert-Bu | 4-ClC₆H₄ | 150–2 | | | | | B |
| 56 | CO₂Me | tert-Bu | 4-HOC₆H₄ | 198–9 | | | | | B |
| 57 | CO₂Me | tert-Bu | 4-H₂NC₆H₄ | | 0.06 | 20% EtOAc/ 80% hex | | | C |
| 58 | CO₂Me | tert-Bu | 4-EtC₆H₄ | | | | 361 (M + H) | FAB | B |

TABLE 1-continued

3-Urido Thiophenes

| # | R² | R⁵ | A | mp (° C.) | TLC (R_f) | TLC Conditions | MS | MS Source | Method |
|---|---|---|---|---|---|---|---|---|---|
| 67 | CO₂Me | tert-Bu | 5-methyl-naphthalen-1-ol (1-OH) | 131–5 | 0.30 | 30% EtOAc/ 70% hex | 399 (M + H) | FAB | B |
| 68 | CO₂Me | tert-Bu | 5-methyl-naphthalen-2-ol | 112 | 0.41 | 35% EtOAc/ 65% hex | 399 (M + H) | FAB | B |
| 69 | CO₂Me | tert-Bu | 5-methyl-1-methoxynaphthalene | 110 | 0.37 | 25% EtOAc/ 65% hex | 399 (M + H) | FAB | B |
| 70 | CO₂Me | tert-Bu | 3-MeO₂CC₆H₄ | | 0.24 | 20% Et₂O/ 80% pet ether | 405 (M + H) | EI | B |
| 71 | CO₂Me | tert-Bu | 2,3-Cl₂C₆H₃ | | 0.44 | 20% Et₂O/ 80% pet ether | 401 (M + H) | CI | B |
| 76 | CO₂Me | tert-Bu | 2,3-dichloro-4-methylphenol | | 0.11 | 20% Et₂O/ 80% pet ether | 417 (M + H) | EI | B |
| 22 | C(O)NHMe | tert-Bu | 4-MeC₆H₄ | 202–4 | | | | | F or G |
| 23 | C(O)NHMe | tert-Bu | 4-EtC₆H₄ | 101–4 | 0.18 | 20% EtOAc/ 80% hex | 360 (M + H) | FAB | G |
| 24 | C(O)NHMe | tert-Bu | 4-iPrC₆H₄ | 113–20 | 0.20 | 20% EtOAc/ 80% hex | 374 (M + H) | FAB | G |
| 25 | C(O)NHMe | tert-Bu | 4-FC₆H₄ | 203–4 | 0.61 | 5% MeOH/ 95% CH₂Cl₂ | 349 (M⁺) | EI | F or G |
| 26 | C(O)NHMe | tert-Bu | 3,4-Me₂C₆H₃ | 180–2 | | | | | G |
| 27 | C(O)NHMe | tert-Bu | 2,4-Me₂C₆H₃ | 195–6 | | | 359 (M⁺) | EI | G |
| 28 | C(O)NHMe | tert-Bu | 3-Cl-4-MeC₆H₃ | 178–9 | | | 379 (M⁺) | EI | G |

TABLE 1-continued

3-Urido Thiophenes

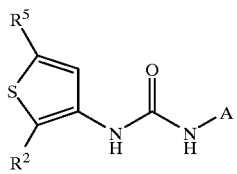

| # | $R^2$ | $R^5$ | A | mp (° C.) | TLC ($R_f$) | TLC Conditions | MS | MS Source | Method |
|---|---|---|---|---|---|---|---|---|---|
| 29 | C(O)NHMe | tert-Bu | 3-F-4-MeC$_6$H$_3$ | 182–3 | | | 364 (M + H) | FAB | G |
| 30 | C(O)NHMe | tert-Bu | 3-Cl-4-FC$_6$H$_3$ | 203–4 | | | 386 (M + H) | FAB | G |
| 31 | C(O)NHMe | tert-Bu | 2,4-F$_2$C$_6$H$_3$ | 213–5 | | | | | G |
| 59 | C(O)NHMe | tert-Bu | 3,4-F$_2$C$_6$H$_3$ | | | | 368 (M + H) | FAB | G |
| 60 | C(O)NHMe | tert-Bu | 2-F-4-MeC$_6$H$_3$ | | | | 364 (M + H) | FAB | G |
| 61 | C(O)NHMe | tert-Bu | 2-Cl-4-MeC$_6$H$_3$ | | | | 380 (M + H) | FAB | G |
| 62 | C(O)NHMe | tert-Bu | 2,3,4-Me$_3$C$_6$H$_2$ | | 0.88 | 50% EtOAc/ 50% hex | 374 (M + H) | FAB | G |
| 63 | C(O)NHMe | tert-Bu | 3-Me-4-FC$_6$H$_3$ | | | | 364 (M + H) | FAB | G |
| 64 | C(O)NHMe | tert-Bu | 2-Cl-4-FC$_6$H$_3$ | | | | 384 (M + H) | FAB | G |
| 65 | C(O)NHMe | tert-Bu | 2-Me-4-FC$_6$H$_3$ | | | | 364 (M + H) | FAB | G |
| 66 | CO$_2$H | tert-Bu | 3,4-Cl$_2$C$_6$H$_3$ | | | | 387 (M + H) | HPLC ES-MS | R |

TABLE 2

3-Urido Furans

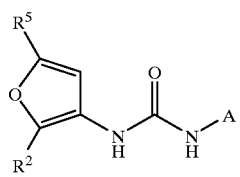

| # | $R^2$ | $R^5$ | A | mp (° C.) | TLC ($R_f$) | TLC Conditions | MS | MS Source | Method |
|---|---|---|---|---|---|---|---|---|---|
| 32 | CO$_2$Me | tert-Bu | 4-MeC$_6$H$_4$ | 78–9 | 0.46 | 20% EtOAc/ 80% hex | 331 (M + H) | FAB | K, L-1 or L-2 |
| 33 | CO$_2$Me | tert-Bu | 4-FC$_6$H$_4$ | 81–2 | 0.37 | 20% EtOAc/ 80% hex | 335 (M + H) | FAB | L-1 or L-2 |
| 34 | CO$_2$Me | tert-Bu | 2,3-Cl$_2$C$_6$H$_4$ | 195–7 | 0.58 | 20% EtOAc/ 80% hex | 385 (M + H) | HPLC ES-MS | L-1 or L-2 |
| 72 | CO$_2$Me | tert-Bu | 3,4-Cl$_2$C$_6$H$_4$ | 83–8 (dec) | 0.19 | 10% EtOAc/ 90% hex | 385 (M + H) | FAB | L-1 or L-2 |
| 35 | C(O)NHMe | tert-Bu | 4-MeC$_6$H$_4$ | 190–3 | 0.25 | 20% EtOAc/ 80% hex | 330 (M + H) | FAB | M |
| 36 | C(O)NHMe | tert-Bu | 4-FC$_6$H$_4$ | 109–11 | 0.21 | 20% EtOAc/ 80% hex | 334 (M + H) | FAB | M |

TABLE 3

3-Urido Pyrroles

| # | R[1] | R[2] | R[5] | A | mp (° C.) | MS | MS Source | Method |
|---|---|---|---|---|---|---|---|---|
| 37 | H | CO$_2$Me | tert-Bu | C$_6$H$_5$ | 262–3 (dec) | 316 (M + H) | FAB | N-1 or N-2 |
| 38 | H | CO$_2$Me | tert-Bu | 4-MeC$_6$H$_4$ | 257–8 | 330 (M + H) | FAB | N-1 or N-2 |
| 39 | H | CO$_2$Me | tert-Bu | 3,4-Cl$_2$C$_6$H$_3$ | 177–8 | 384 (M + H) | FAB | N-1 or N-2 |
| 73 | H | CO$_2$Me | tert-Bu | 2,3-Cl$_2$C$_6$H$_3$ | 194–6 | 384 (M + H) | FAB | N-2 |
| 74 | H | CO$_2$Me | tert-Bu | (1-methylnaphthyl) | 195–6 | 366 (M + H) | FAB | N-2 |
| 75 | H | CO$_2$Me | tert-Bu | 4-FC$_6$H$_4$ | 214–46 | | | N-2 |
| 76 | H | CO$_2$Me | tert-Bu | (2-Cl-5-Me-3-CF$_3$-C$_6$H$_2$) | 169–70 | 418 (M + H) | FAB | N-2 |
| 78 | H | CO$_2$Me | tert-Bu | 2,4-F$_2$C$_6$H$_3$ | 233–4 | 352 (M + H) | FAB | N-2 |
| 79 | H | CO$_2$Me | tert-Bu | 3-FC$_6$H$_4$ | 245–6 (dec) | 333 (M$^+$) | EI | N-2 |
| 80 | H | CO$_2$Me | tert-Bu | 2-ClC$_6$H$_4$ | 252–3 | 350 (M + H) | FAB | N-2 |
| 81 | H | CO$_2$Me | tert-Bu | 3,5-Cl$_2$C$_6$H$_3$ | 169–70 | 384 (M + H) | FAB | N-2 |
| 82 | H | CO$_2$Me | tert-Bu | 3-ClC$_6$H$_4$ | 177–8 | 350 (M + H) | FAB | N-2 |
| 83 | H | CO$_2$Me | tert-Bu | 2-FC$_6$H$_4$ | 242–3 | 336 | FAB | N-2 |
| 84 | H | CO$_2$Me | tert-Bu | (2,5-dimethylthiophene) | 233–4 | 336 (M + H) | FAB | N-2 |
| 85 | H | CO$_2$Me | tert-Bu | 3,5-Me$_2$C$_6$H$_3$ | 228–9 | 344 (M + H) | FAB | N-2 |
| 86 | H | CO$_2$Me | tert-Bu | 2-MeC$_6$H$_4$ | 191–2 | 330 (M + H) | FAB | N-2 |
| 87 | H | CO$_2$Me | tert-Bu | (5-methylindole) | 242–3 | 355 (M + H) | FAB | N-2 |

TABLE 3-continued

3-Urido Pyrroles

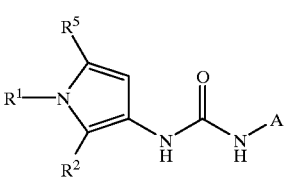

| # | R¹ | R² | R⁵ | A | mp (° C.) | MS | MS Source | Method |
|---|----|----|----|---|-----------|-----|-----------|--------|
| 88 | H | CO₂Me | tert-Bu | 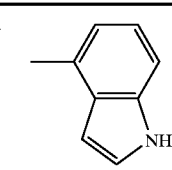 | 245–6 | 355 (M + H) | FAB | N-2 |
| 89 | H | CO₂Me | tert-Bu | 3-MeC₆H₄ | 191–2 | 330 (M + H) | FAB | N-2 |
| 90 | H | CO₂Me | tert-Bu | 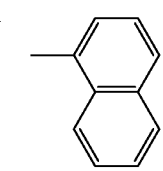 | 210–1 | 366 (M + H) | FAB | N-2 |
| 91 | H | CO₂Me | tert-Bu | 3-Cl-4-FC₆H₃ | 193–4 | 368 (M + H) | FAB | N-2 |
| 92 | H | CO₂Me | tert-Bu | 3-Cl-4-MeC₆H₃ | 185–6 | 364 (M + H) | FAB | N-2 |
| 93 | H | CO₂Me | tert-Bu | 2-Me-4-ClC₆H₃ | 226–7 | 364 (M + H) | FAB | N-2 |
| 94 | H | CO₂Me | tert-Bu | 2-Me-5-ClC₆H₃ | 196–7 | | | N-2 |
| 95 | H | CO₂Me | tert-Bu | 2,4-Me₂C₆H₃ | 258–9 | | | N-2 |
| 96 | H | CO₂Me | tert-Bu | 3,4-Me₂C₆H₃ | 195–6 | | | N-2 |
| 97 | H | CO₂Me | tert-Bu | 2,5-F₂C₆H₃ | 228–30 | | | N-2 |
| 98 | H | CO₂Me | tert-Bu | 4-Me₂NC₆H₄ | 235–7 | 358 (M⁺) | EI | N-2 |
| 99 | H | CO₂Me | tert-Bu | 4-H₂NC₆H₄ | 242–4 | 331 (M + H) | FAB | N-2 |
| 100 | H | CO₂Me | tert-Bu | 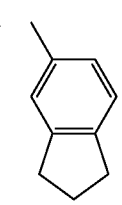 | 192–4 | 355 (M + H) | EI | N-2 |
| 105 | H | CO₂Me | tert-Bu | 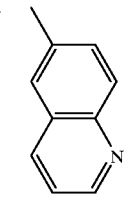 | 230–1 | 367 (M + H) | FAB | N-2 |
| 106 | H | CO₂Me | tert-Bu | 2-BrC₆H₄ | 253–4 | 394 (M + H) | FAB | N-2 |
| 107 | H | CO₂Me | tert-Bu | 4-BrC₆H₄ | 248–9 | 394 (M + H) | FAB | N-2 |
| 108 | H | CO₂Me | tert-Bu | 2,4-Cl₂C₆H₃ | 200–1 | 383 (M⁺) | EI | N-2 |

TABLE 3-continued

3-Urido Pyrroles

| # | R¹ | R² | R⁵ | A | mp (° C.) | MS | MS Source | Method |
|---|----|----|----|---|-----------|----|-----------|--------|
| 109 | H | $CO_2Me$ | tert-Bu | 4-tert-Bu$C_6H_4$ | 188–91 | 372 (M + H) | FAB | N-2 |
| 110 | H | $CO_2Me$ | tert-Bu | 4-iPrO$C_6H_4$ | 139–40 | 374 (M + H) | FAB | N-2 |
| 111 | H | $CO_2Me$ | tert-Bu | 4-Cl$C_6H_4$ | 257–8 (dec) | 350 (M + H) | FAB | N-2 |
| 112 | H | $CO_2Me$ | tert-Bu | 3-$F_3$C$C_6H_4$ | 138–9 | 384 (M + H) | FAB | N-2 |
| 113 | H | C(O)NHMe | tert-Bu | 4-Me$C_6H_4$ | 164–6 | 329 (M + H) | FAB | N-3 |
| 114 | H | C(O)NHMe | tert-Bu | 2,3-$Cl_2C_6H_3$ | 227–8 | 383 (M + H) | FAB | N-3 |
| 115 | H | C(O)NHMe | tert-Bu | 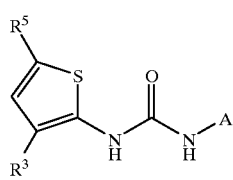 | 177–8 | 365 (M + H) | FAB | N-3 |
| 40 | Me | $CO_2Me$ | tert-Bu | 4-Me$C_6H_4$ | 171–2 | 343 ($M^+$) | EI | O |
| 101 | Me | $CO_2Me$ | tert-Bu | 2,3-$Cl_2C_6H_4$ | 94–7 | 398 (M + H) | FAB | O |
| 102 | Me | $CO_2Me$ | tert-Bu |  | 178–9 | 380 (M + H) | FAB | O |
| 103 | Me | $CO_2Me$ | tert-Bu | $C_6H_5$ | 175–6 | 330 (M + H) | FAB | O |
| 104 | Me | $CO_2Me$ | tert-Bu | 4-F$C_6H_4$ | 211–2 | 347 ($M^+$) | EI | O |

TABLE 4

2-Urido Thiophenes

| # | R³ | R⁵ | A | mp (° C.) | TLC ($R_f$) | TLC Conditions | MS | MS Source | Method |
|---|----|----|---|-----------|-------------|----------------|----|-----------|--------|
| 41 | $CO_2Me$ | iPr | $C_6H_5$ | 64–5 |  |  | 319 (M + H) | FAB | Q |

TABLE 4-continued

2-Urido Thiophenes

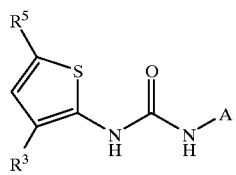

| # | R³ | R⁵ | A | mp (° C.) | TLC (R_f) | TLC Conditions | MS | MS Source | Method |
|---|---|---|---|---|---|---|---|---|---|
| 42 | CO₂Me | iPr | 4-MeC₆H₄ | 49–51 | | | 333 (M⁺) | EI | Q |
| 43 | CO₂Me | tert-Bu | C₆H₅ | 80–2 | | | 333 (M⁺) | EI | P |
| 44 | CO₂Me | tert-Bu | 4-MeC₆H₄ | 109–11 | | | | | P |
| 116 | CO₂Me | —CH₂-C(CH₃)₃ | 4-MeC₆H₄ | 141–2 | | | | | Q |
| 117 | CO₂Me | tert-Bu | 3-F-4-MeO-C₆H₃ (Me, OMe, F substituted phenyl) | | 0.20 | 20% Et₂O/ 80% pet ether | 381 (M + H) | EI | S |
| 118 | CO₂Me | tert-Bu | 2,3-Cl₂C₆H₃ | | 0.45 | 20% Et₂O/ 80% pet ether | 401 (M + H) | CI | S |
| 119 | C(O)NH₂ | tert-Bu | 4-MeC₆H₄ | | 0.19 | 50% Et₂O/ 50% pet ether | 332 (M + H) | CI | U |
| 120 | CO₂Me | tert-Bu | 2,3-Cl₂-4-OH-6-Me-C₆H (Me, OH, Cl, Cl substituted phenyl) | | 0.13 | 20% Et₂O/ 80% pet ether | 417 (M + H) | EI | S |
| 121 | CO₂Me | tert-Bu | 2-MeC₆H₄ | | 0.32 | 20% Et₂O/ 80% pet ether | 347 (M + H) | HPLC ES-MS | S |
| 122 | CO₂Me | tert-Bu | 3-MeC₆H₄ | | 0.34 | 20% Et₂O/ 80% pet ether | 347 (M + H) | HPLC ES-MS | S |
| 123 | CO₂Me | tert-Bu | 4-iPrC₆H₄ | | 0.38 | 20% Et₂O/ 80% pet ether | 375 (M + H) | HPLC ES-MS | S |
| 124 | CO₂Me | tert-Bu | 3-MeOC₆H₄ | | 0.24 | 20% Et₂O/ 80% pet ether | 363 (M + H) | HPLC ES-MS | S |
| 125 | CO₂Me | tert-Bu | 4-MeOC₆H₄ | | 0.18 | 20% Et₂O/ 80% pet ether | 363 (M + H) | HPLC ES-MS | S |
| 126 | CO₂Me | tert-Bu | 4-n-BuOC₆H₄ | | 0.32 | 20% Et₂O/ 80% pet ether | 405 (M + H) | HPLC ES-MS | S |
| 127 | CO₂Me | tert-Bu | 2-HOC₆H₄ | | 0.49 | 50% Et₂O/ 50% pet ether | 349 (M + H) | HPLC ES-MS | S |
| 128 | CO₂Me | tert-Bu | 3-HOC₆H₄ | | 0.43 | 50% Et₂O/ 50% pet ether | 349 (M + H) | HPLC ES-MS | S |
| 129 | CO₂Me | tert-Bu | 4-HOC₆H₄ | | 0.38 | 50% Et₂O/ 50% pet ether | 349 (M + H) | HPLC ES-MS | S |
| 130 | CO₂Me | tert-Bu | 2,4-Me₂C₆H₃ | | 0.34 | 20% Et₂O/ 80% pet ether | 361 (M + H) | HPLC ES-MS | S |
| 131 | CO₂Me | tert-Bu | 2,5-Me₂C₆H₃ | | 0.36 | 20% Et₂O/ 80% pet ether | 361 (M + H) | HPLC ES-MS | S |
| 132 | CO₂Me | tert-Bu | 3,4-Me₂C₆H₃ | | 0.34 | 20% Et₂O/ 80% pet ether | 361 (M + H) | HPLC ES-MS | S |
| 133 | CO₂Me | tert-Bu | 3,5-Me₂C₆H₃ | | 0.36 | 20% Et₂O/ 80% pet ether | 361 (M + H) | HPLC ES-MS | S |
| 134 | CO₂Me | tert-Bu | 2,3-F₂C₆H₃ | | 0.44 | 20% Et₂O/ 80% pet ether | 369 (M + H) | HPLC ES-MS | S |
| 135 | CO₂Me | tert-Bu | 2,6-F₂C₆H₃ | | 0.25 | 20% Et₂O/ 80% pet ether | 369 (M + H) | HPLC ES-MS | S |
| 136 | CO₂Me | tert-Bu | 2-FC₆H₄ | | 0.42 | 20% Et₂O/ 80% pet ether | 351 (M + H) | HPLC ES-MS | S |
| 137 | CO₂Me | tert-Bu | 3-FC₆H₄ | | 0.31 | 20% Et₂O/ 80% pet ether | 351 (M + H) | HPLC ES-MS | S |

TABLE 4-continued

2-Urido Thiophenes

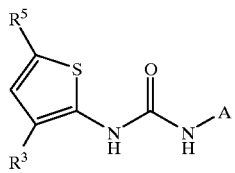

| # | R³ | R⁵ | A | mp (° C.) | TLC (R_f) | TLC Conditions | MS | MS Source | Method |
|---|---|---|---|---|---|---|---|---|---|
| 138 | CO₂Me | tert-Bu | 4-FC₆H₄ | | 0.31 | 20% Et₂O/ 80% pet ether | 351 (M + H) | HPLC ES-MS | S |
| 139 | CO₂Me | tert-Bu | 2-ClC₆H₄ | | 0.41 | 20% Et₂O/ 80% pet ether | 367 (M + H) | HPLC ES-MS | S |
| 140 | CO₂Me | tert-Bu | 3-ClC₆H₄ | | 0.31 | 20% Et₂O/ 80% pet ether | 367 (M + H) | HPLC ES-MS | S |
| 141 | CO₂Me | tert-Bu | 2,4-F₂C₆H₃ | | 0.40 | 20% Et₂O/ 80% pet ether | 369 (M + H) | HPLC ES-MS | S |
| 142 | CO₂Me | tert-Bu | 4-Me₂NC₆H₃ | | 0.45 | 50% Et₂O/ 50% pet ether | 376 (M + H) | EI | T |
| 143 | CO₂Me | tert-Bu | 2,5-F₂C₆H₃ | | 0.39 | 20% Et₂O/ 80% pet ether | 369 (M + H) | HPLC ES-MS | S |
| 144 | C(O)NH₂ | tert-Bu | 2,3-Cl₂C₆H₃ | | 0.46 | 40% Et₂O/ 60% pet ether | 386 (M⁺) | EI | U |

TABLE 5

2-Aminomethyl-3-urido Thiophenes

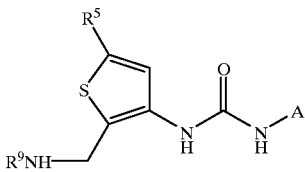

| # | R⁵ | R⁹ | A | mp (° C.) | MS | MS Source | Method |
|---|---|---|---|---|---|---|---|
| 50 | tert-Bu | C(O)CH₃ | 4-MeC₆H₄ | 203–5 | 360 (M + H) | FAB | I |
| 51 | tert-Bu | C(O)CH₂NH₂ | 4-MeC₆H₄ | 93–6 | | | I |
| 52 | tert-Bu | C(O)CH₂NHBOC | 4-MeC₆H₄ | 174–6 | | | I |

Biological Examples

P38 Kinase Assay

The in vitro inhibitory properties of compounds were determined using a p38 kinase inhibition assay. P38 activity was detected using an in vitro kinase assay run in 96-well microtiter plates. Recombinant human p38 (0.5 μg/mL) was mixed with substrate (myelin basic protein, 5 μg/mL) in kinase buffer (25 mM Hepes, 20 mM MgCl₂ and 150 mM NaCl) and compound. One μCi/well of $^{33}$P-labeled ATP (10 μM) was added to a final volume of 100 μL. The reaction was run at 32° C. for 30 min. and stopped with a 1M HCl solution. The amount of radioactivity incorporated into the substrate was determined by trapping the labeled substrate onto negatively charged glass fiber filter paper using a 1% phosphoric acid solution and read with a scintillation counter. Negative controls included substrate plus ATP alone.

All compounds exemplified displayed p38 IC₅₀s of between 1 nM and 10 μM.

LPS Induced TNFα Production in Mice

The in vivo inhibitory properties of selected compounds were determined using a murine LPS induced TNFα production in vivo model. BALB/c mice (Charles River Breeding Laboratories; Kingston, N.Y.) in groups of ten were treated with either vehicle or compound by the route noted. After one hour, endotoxin (E. coli lipopolysaccharide (LPS) 100 μg) was administered intraperitoneally (i.p.). After 90 min, animals were euthanized by carbon dioxide asphyxiation and plasma was obtained from individual animals by cardiac puncture into heparinized tubes. The samples were clarified by centrifugation at 12,500×g for 5 min at 4° C. The supernatants were decanted to new tubes, which were stored as needed at −20° C. TNFα levels in sera were measured using a commercial murine TNF ELISA kit (Genzyme).

The preceding examples can be repeated with similar success by substituting the generically or specifically described reactants and/or operating conditions of this invention for those used in the preceding examples.

What is claimed is:

1. A method for the treatment of a disease, other than cancer, mediated by p38, comprising administering a compound of Formula I

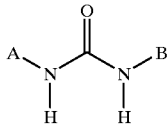

wherein

A is optionally substituted $C_{6-12}$-aryl or $C_{5-12}$-heteroaryl;

B is

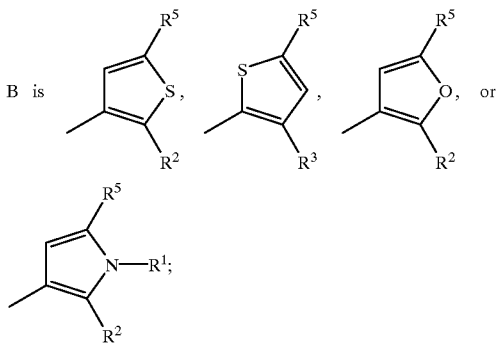

$R^1$ is H or $C_{1-4}$-alkyl;

$R^2$ and $R^3$ are each independently halogen, —COOR$^1$, —CN, —CONR$^7$R$^8$, or —CH$_2$NHR$^9$;

$R^5$ is $C_{3-5}$-alkyl;

$R^6$ is $C_{1-6}$-alkyl;

$R^7$ is hydrogen;

$R^8$ is methyl;

$R^9$ is hydrogen, methyl or —CO—R$^{10}$; and $R^{10}$ is hydrogen or methyl optionally substituted by NR$^6{}_2$ or COOR$^6$.

2. A method according to claim 1, wherein the disease is mediated by a cytokine or protease regulated by p38.

3. A method according to claim 1, wherein A is $C_{6-12}$-aryl or $C_{5-12}$-heteroaryl optionally substituted by $C_{1-4}$-alkyl, $C_{3-6}$-cycloalkyl, halogen, —OH, —OR$^1$, or —NR$^1{}_2$.

4. A method according to claim 1, wherein R$^5$ is isopropyl or tert-butyl.

5. A method according to claim 1, wherein A is phenyl, 1,3,4-thiadiazol-2- or -5-yl, 7-indolyl, or 8-quinolinyl, each optionally substituted by $C_{1-4}$-alkyl, $C_{3-6}$-cycloalkyl, halogen, —OH, —OR$^1$, or —N$^1{}_2$.

6. A method according to claim 1, wherein A is 4-methylphenyl, 4-fluorophenyl, 5-methyl-2-thienyl, 4-methyl-2-thienyl, or 5-cyclopropyl-1,3,4-thiadiazol-2-yl.

7. A method according to claim 1, wherein R$^2$ or R$^3$ is —COOR$^1$ or CH$_2$NHR$^9$, and R$^1$ is $C_{1-4}$-alkyl, R$^7$ is H, and R$^8$ is $C_{1-10}$-alkyl.

8. A method according to claim 1, comprising administering an amount of a compound of Formula I effective to inhibit p38.

9. A method according to claim 2, wherein the disease is mediated by TNFα, MMP-1, MMP-3, IL-1, IL-6, or IL-8.

10. A method according to claim 1, wherein the disease is an inflammatory or immunomodulatory disease.

11. A method according to claim 1, wherein the disease is rheumatoid arthritis, osteoporosis, asthma, septic shock, inflammatory bowel disease, or the result of host-versus-graft reactions.

12. A method according to claim 1, wherein the compound is N-(2-carbomethoxy-5-isopropyl-3-thienyl)-N'-(phenyl)urea; N-(2-carbomethoxy-5-tert-butyl-3-thienyl)-N'-(4-methylphenyl)urea; N-(2-carbomethoxy-5-tert-butyl-3-thienyl)-N'-(4-fluorophenyl)urea; N-(2-carbomethoxy-5-tert-butyl-3-thienyl)-N'-(3-methylphenyl)urea; N-(2-carbomethoxy-5-tert-butyl-3-thienyl)-N'-(5-cyclopropyl-2-thiadiazolyl)urea; N-(2-carbomethoxy-5-tert-butyl-3-thienyl)-N'-(2-aminophenyl)urea; N-(2-carboethoxy-5-tert-butyl-3-thienyl)-N'-(4-methylphenyl)urea; N-(2-(carbo-1-prop-2-enyloxy)-5-tert-butyl-3-thienyl)-N'-(4-methylphenyl)urea; N-(2-(carbo-2-propyloxy)-5-tert-butyl-3-thienyl)-N'-(4-methylphenyl)urea; N-(2-(carbo-1-propyloxy)-5-tert-butyl-3-thienyl)-N'-(4-methylphenyl)urea; N-(2-methylcarbamoyl-5-tert-butyl-3-thienyl)-N'-(4-methylphenyl)urea; N-(2-methylcarbamoyl-5-tert-butyl-3-thienyl)-N'-(4-fluorophenyl)urea; N-(2-methylcarbamoyl)-5-tert-butyl-3-thienyl)-N'-(4-ethylphenyl)urea; N-(2-methylcarbamoyl)-5-tert-butyl-3-thienyl)-N'-(4-isopropylphenyl)urea; N-(2-methylcarbamoyl)-5-tert-butyl-3-thienyl)-N'-(2,4-dimethylphenyl)urea; N-(2-methylcarbamoyl)-5-tert-butyl-3-thienyl)-N'-(3-chloro-4-methylphenyl)urea; N-(2-methylcarbamoyl)-5-tert-butyl-3-thienyl)-N'-(3-fluoro-4-methylphenyl)urea; N-(2-methylcarbamoyl)-5-tert-butyl-3-thienyl)-N'-(3-chloro-4-fluorophenyl)urea; N-(2-carboxy-5-tert-butyl-3-thienyl)-N'-(4-methylphenyl)urea; N-(2-(N-glycylaminomethyl)-5-tert-butyl-3-thienyl)-N'-(4-methylphenyl)urea; N-(2-(N-(N-carbo-tert-butoxyglycyl)aminomethyl)-5-tert-butyl-3-thienyl)-N'-(4-methylphenyl)urea; N-(2-(N-acetylaminomethyl)-5-tert-butyl-3-thienyl)-N'-(4-methylphenyl)urea; N-(2-carbomethoxy-5-tert-butyl-3-thienyl)-N'-(4-methyl-2-thienyl)urea; or N-(2-carbomethoxy-5-tert-butyl-3-thienyl)-N'-(5-methyl-2-thienyl)urea.

13. A method according to claim 1, wherein the compound is N-(2-carbomethoxy-5-tert-butyl-3-furyl)-N'-(4-methylphenyl)urea; N-(2-carbomethoxy-5-tert-butyl-3-furyl)-N'-(4-fluorophenyl)urea; N-(2-carbomethoxy-5-tert-butyl-3-furyl)-N'-(2,3-dichlorophenyl)urea; N-(2-methylcarbamoyl-5-tert-butyl-3-furyl)-N'-(4-fluorophenyl)urea; or N-(2-methylcarbamoyl-5-tert-butylfuryl)-N'-(4-methylphenyl)urea.

14. A method according to claim 1, wherein the compound is N-(2-carbomethoxy-5-tert-butyl-3-pyrrolyl)-N'-(4-methylphenyl)urea; N-(2-carbomethoxy-5-tert-butyl-3-pyrrolyl)-N'-(phenyl)urea; N-(2-carbomethoxy-5-tert-butyl-3-pyrrolyl)-N'-(2,3-dichlorophenyl)urea; or N-(N-methyl-2-carbomethoxy-5-tert-butyl-3-pyrrolyl)-N'-(5-methyl-2-thienyl)urea.

15. A method according to claim 1, wherein the compound is N-(3-carbomethoxy-5-tert-butyl-2-thienyl)-N'-(4-methylphenyl)urea; N-(3-carbomethoxy-5-tert-butyl-2-thienyl)-N'-(phenyl)urea; N-(3-carbomethoxy-5-isopropyl-2-thienyl)-N'-(4-methylphenyl)urea; or N-(3-carbomethoxy-5-isopropyl-2-thienyl)-N'-(phenyl)urea.

16. A method according to claim 1, wherein the compound is N-(2-methylcarbamoyl-5-tert-butyl-3-furyl)-N'-(3,4-dichlorophenyl)urea; N-(2-carbomethoxy-5-tert-butyl-3- pyrrolyl)-N'-(2,3-dichlorophenyl)urea; N-(2-carbomethoxy-5-tert-butyl-3-pyrrolyl)-N'-(3,4-dichlorophenyl)urea; N-(2-carbomethoxy-5-tert-butyl-3-pyrrolyl)-N'-(1-naphthyl)urea; N-(2-carbomethoxy-5-tert-butyl-3-pyrrolyl)-N'-(2-naphthyl)urea; N-(2-carbomethoxy-5-tert-butyl-3-pyrrolyl)-N'-(3-chloro-4-fluorophenyl)urea; N-(2-carbomethoxy-5-tert-butyl-3-pyrrolyl)-N'-(3-chloro-4-methylphenyl)urea; N-(2-methylcarbamoyl-5-tert-butyl-3-pyrrolyl)-N'-(2,3-dichlorophenyl)urea; N-(2-methylcarbamoyl-5-tert-butyl-3-pyrrolyl)-N'-(1-naphthyl)urea; N-(N-methyl-2-carbomethoxy-5-tert-butyl-3-pyrrolyl)-N'-(1-naphthyl)urea; N-(N-methyl-2-carbomethoxy-5-tert-butyl-3-pyrrolyl)-N'-(2,3-dichlorophenyl)urea; N-(N-methyl-2-carbomethoxy-5-tert-butyl-3-pyrrolyl)-N'-(4-methylphenyl)urea; N-(N-methyl-2-carbomethoxy-5-tert-butyl-3-pyrrolyl)-N'-(phenyl)urea; N-(3-carbomethoxy-5-tert-butyl-2-thienyl)-N'-(3-methylphenyl)urea; N-(3-carbomethoxy-5-tert-butyl-2-thienyl)-N'-(2,3-dichlorophenyl)urea; N-(3-carbomethoxy-5-tert-butyl-2-thienyl)-N'-(2,3-dichloro-4-hydroxyphenyl)urea; N-(3-carbomethoxy-5-tert-butyl-2-thienyl)-N'-(3-methoxyphenyl)urea; or N-(3-carbamoyl-5-tert-butyl-2-thienyl)-N'-(4-methylphenyl)urea.

17. A method according to claim 1, wherein B is

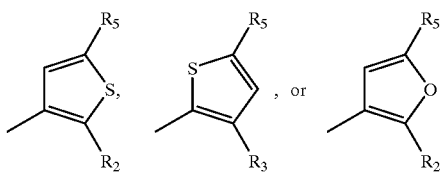

18. A method according to claim 1, wherein B is

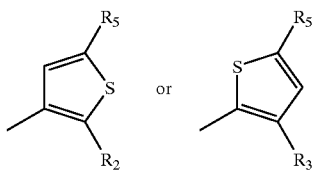

* * * * *